(12) United States Patent
Lambrecht et al.

(10) Patent No.: US 9,567,618 B2
(45) Date of Patent: Feb. 14, 2017

(54) MICROORGANISMS AND METHODS FOR PRODUCING SUBSTITUTED PHENOLS

(75) Inventors: Stefan Lambrecht, Hehlen (DE);
Jens-Michael Hilmer, Holzminden (DE); Manuel Pesaro, Holzminden (DE); Jens Kroll, Kamen (DE); Gunda Hansen, Mildstedt (DE); Alexander Steinbüchel, Altenberge (DE);
Christian Fleige, Dortmund (DE)

(73) Assignee: SYMRISE AG, Holzminden (DE)

( * ) Notice: Subject to any disclaimer, the term of this patent is extended or adjusted under 35 U.S.C. 154(b) by 126 days.

(21) Appl. No.: 13/985,261

(22) PCT Filed: Jun. 18, 2012

(86) PCT No.: PCT/EP2012/061600
§ 371 (c)(1),
(2), (4) Date: Aug. 13, 2013

(87) PCT Pub. No.: WO2012/172108
PCT Pub. Date: Dec. 20, 2012

(65) Prior Publication Data
US 2014/0087428 A1    Mar. 27, 2014

Related U.S. Application Data

(60) Provisional application No. 61/498,223, filed on Jun. 17, 2011.

(30) Foreign Application Priority Data

Jun. 17, 2011    (EP) .................... 11170461

(51) Int. Cl.
| | | |
|---|---|---|
| C12N 1/12 | (2006.01) |
| C12Q 1/68 | (2006.01) |
| C12N 9/04 | (2006.01) |
| C12N 1/20 | (2006.01) |
| C12N 15/00 | (2006.01) |
| C07H 21/04 | (2006.01) |
| C12P 7/42 | (2006.01) |
| C12P 1/06 | (2006.01) |
| C12P 7/00 | (2006.01) |
| C12P 19/32 | (2006.01) |
| C12N 9/02 | (2006.01) |
| C12P 7/22 | (2006.01) |
| C12P 7/24 | (2006.01) |

(52) U.S. Cl.
CPC .............. *C12P 19/32* (2013.01); *C12N 9/0008* (2013.01); *C12P 7/22* (2013.01); *C12P 7/24* (2013.01); *C12P 7/42* (2013.01); *C12Y 102/01067* (2013.01); *Y02P 20/52* (2015.11)

(58) Field of Classification Search
CPC ....... C12N 9/0008; C12N 15/76; C12N 15/09; C12P 7/02
See application file for complete search history.

(56) References Cited

FOREIGN PATENT DOCUMENTS

| | | |
|---|---|---|
| EP | 0761817 A2 | 3/1997 |
| EP | 0885968 | 12/1998 |
| EP | 0885968 A1 | 12/1998 |
| WO | 0026355 A2 | 5/2000 |

OTHER PUBLICATIONS

European Patent Search Report dated Oct. 22, 2012 for priority application PCT/EP2012/061600.
International Search Report dated Oct. 22, 2012.
International Preliminary Report on Patentability dated Dec. 17, 2013.
Rainer Plaggenborg, et al., "Potential of Rhodococcus Strains for Biotechnological Vanillin Production from Ferulic Acid and Eugenol," Applied Microbiology and Biotechnology, vol. 72, No. 4, Jan. 19, 2006, pp. 745-755.
Mamoru Yamada, et al., "Biotransformation of Isoeugenol to Vanillin by Pseudomonas Putida IE27 Cells," Applied Microbiology and Biotechnology, vol. 73x, No. 5, Aug. 30, 2006, pp. 1025-1030.
Muheim A., et al., "Towards a High-Yield Bioconversion of Ferulic Acid to Vanillin," Applied Microbiology and Biotechnology, vol. 51, No. 4, Apr. 1999, pp. 456-461.
Database Genseq (Online), Fischbach, M., et al., Vanillin Dehydrogenase (Streptomyces Himastatinicus ATCC 53653]; Oct. 26, 2010, Database accession No. ZP_07300335; XP002684680.
Overhage, J., et al., "Harnessing Eugenol as a Substrate for Production of Aromatic Compounds with Recombinant Strains of Amycolatopsis sp. HR167," Journal of Biotechnology, Elsevier Science Publishers, Amsterdam, NL. vol. 125, No. 3, Sep. 17, 2006, pp. 369-376.
Di Gioia Diana, et al., "Metabollic Engineering of Pseudomonas Fluorescens for the Production of Vanillin from Ferulic Acid," Journal of Biotechnology, Dec. 20, 2010, vol. 156, No. 4, pp. 309-316.
Gounaris, et al., "Biotechnology for the Production of Essential Oils, Flavours, and Volatile Isolates. A Review", Flavour and Fragrance Journal, vol. 25, No. 5, Sep. 2010, pp. 367-386.
Database UniProt, Feasey, et al., Subname: Full = Benzaldehyde Dehydrogenase [NAD+], XP002684681, May 3, 2011.
Database UniProt, Sun, et al., "Subname: Full=Aldehyde Dehydrogenase," XP002684682, Aug. 10, 2010.
Database UniProt Muzny, et al., "Subname: Full=Benzaldewhyde Dehydrogenase; EC=1.2.1.28," XP002684683, Jul. 13, 2010.
Sutherland, J. B. et al., "Metabolism of cinnamic, p-coumaric, and ferulic acids by *Streptomyces setonir* ", Can. J. Microbiol, vol. 29, pp. 1253-1257, (1983).
Plaggenborg, R. et al., "Potential of *Rhodococcus* strains for biotechnological vanillin production from ferulic acid and eugenol", Appl Microbiol Biotechnol, vol. 72, pp. 745-755, (2006).

(Continued)

Primary Examiner — Yong Pak
(74) Attorney, Agent, or Firm — Polsinelli PC

(57) ABSTRACT

The present invention is concerned with methods for producing vanillin, feroyl-CoA, ferulic acid, coniferyl aldehyde and/or coniferyl alcohol. Also, the invention relates to microorganisms useful in such production method, and to the construction of such microorganisms.

15 Claims, 9 Drawing Sheets

(56) References Cited

OTHER PUBLICATIONS

Pometto, A.L. and Crawford, D.L., "Whole-cell Bioconversion of Vanillin to Vanillic Acid by *Streptomyces viridosporus*", Applied and Environmental Microbiology, vol. 45, No. 5, pp. 1582-1585, (1983).

Ghosh, S. et al., Microbial transformation of ferulic acid to vanillic acid by *Streptomyces sannanensis* MTCC 6637, J Ind Microbiol Biotechnol, vol. 34, pp. 131-138, (2007).

Ding, W., et al., "Functional characterization of a vanillin dehydrogenase in Corynebacterium glutamicum," Scientific Reports, 5:8044, DOI: 10. 1038/srep08044, pp. 1-7 (2015).

Martinez-Cuesta, Maria-Del-Carmen, et al., "Functional analysis of the vanillin pathway in a vdh-negative mutant strain of Pseudomonas fluorescens AN103," Enzyme and Microbial Technology 37 (2005) 131-138.

Sainsbury, Paul D., et al., "Breaking Down Lignin to High-Value Chemicals: The Conversion of Lignocellulose to Vanillin in a Gene Deletion Mutant of Rhodococcus jostii RHA1," ACS Chem. Biol., 2013, 8, pp. 2151-2156.

gtgagctttctcgacgacgagaagtggaccggacgcgtcttcaccggcagctgggagcgcgcggcgggcggcgacgcg
gccgtcatcgagcccgcgaccggcgacgaactggggcgcgtcggcatcgcctcgccccaggacctggcggcctccgcg
gccaaggcggccgaggcgcagcgcgcctgggcggcgacctccttccaagaacgcgccgcggtcctgcgccgcgccgg
cgacctgtggcagcagcacgccgccgagctgaaggactggctgatccgcgagtcgggcagcatcccggcaaggccga
cttcgaactgcacgtcgccgcgcaggagtgctacgaggccgccgcgctgccctcccacccgacgggtgaggtcctgccga
gcgaggcgccgcggctgagcatggcccgccgcgtgcccgccggcgtggtcggcgtgatcgcgccgttcaacgcgccgct
gatcctgtcgatccgctcggtcgcgccggcgctggcgctgggcaacagcgtcgtgctcaagccggaccccccgcaccgcgg
tctgcggtggcgtggcgctggccagggtcttcgaggaggccgggctgcccgccggggtcctgcacgtgctgccgggcggc
ccggacgtcggcgccgcgctggtcgaggacaagcacgtccgcgtcatctcgttcaccggatcgaccgccgcgggccgcg
cggtcggcgagtccgcgggccgccacctcaagcgcgcccacctggaactgggcggcaactcggcgctgatcgtgctcga
cgacgccgacctggagcaggcgatgagcgccgccgcgtggggctcgttcttccaccagggccagatctgcatgaccacc
gggcggcacctggtgcacgcctcactctacgacgaatacgtggaccgcctggcggacaaggccagccacctgccggtgg
gcaacccgttcaccgagcaggtcgcgctcggcccgatcatcgacgccaagcagcgcgacaagatccacggcctggtga
cgtccagtgtggacgccggcgcgaaggtcgccgcgggcggcacctacgaggacctcttctaccgcgccaccgtgctcgcc
ggcgcggggcccctcggtgcccgcctacgaccaggaggtgttcggcccggtcgccccggtcgcgaagttcaccagcctgg
acgaggccgcgaagctcgcgtcggagagcgagtacgggctgtcgctgggcatcatcaccgcggacgtggcgaagggac
tggcgctggccgaccgcatcccgaccggcatcgcgcacatcaacgaccagacggtcaacgacgaggcgctggccccgt
tcggcggcgtgttcgactccggcaccggctcccgcttcggcgggccggccgcgaacatcgaggcgttcaccgagacccgc
tgggtcacgatgcgcggcgacgtcgccggctacccgttctga

Fig. 2

VSFLDDEKWTGRVFTGSWERAAGGDAAVIEPATGDELGRVGIASPQDLAASAAKAAEA
QRAWAATSFQERAAVLRRAGDLWQQHAAELKDWLIRESGSIPGKADFELHVAAQECYE
AAALPSHPTGEVLPSEAPRLSMARRVPAGVVGVIAPFNAPLILSIRSVAPALALGNSVVLK
PDPRTAVCGGVALARVFEEAGLPAGVLHVLPGGPDVGAALVEDKHVRVISFTGSTAAGR
AVGESAGRHLKRAHLELGGNSALIVLDDADLEQAMSAAAWGSFFHQGQICMTTGRHLV
HASLYDEYVDRLADKASHLPVGNPFTEQVALGPIIDAKQRDKIHGLVTSSVDAGAKVAAG
GTYEDLFYRATVLAGAGPSVPAYDQEVFGPVAPVAKFTSLDEAAKLASESEYGLSLGIIT
ADVAKGLALADRIPTGIAHINDQTVNDEALAPFGGVFDSGTGSRFGGPAANIEAFTETRW
VTMRGDVAGYPF

Fig. 3

SEQUENCE LISTING

```
<160> NUMBER OF SEQ ID NOS: 16

<210> SEQ ID NO 1
<211> LENGTH: 486
<212> TYPE: PRT
<213> ORGANISM: Actinomycetales

<400> SEQUENCE: 1

Val Ser Phe Leu Asp Asp Glu Lys Trp Thr Gly Arg Val Phe Thr Gly
1               5                  10                  15

Ser Trp Glu Arg Ala Ala Gly Gly Asp Ala Ala Val Ile Glu Pro Ala
            20                  25                  30

Thr Gly Asp Glu Leu Gly Arg Val Gly Ile Ala Ser Pro Gln Asp Leu
        35                  40                  45

Ala Ala Ser Ala Ala Lys Ala Ala Glu Ala Gln Arg Ala Trp Ala Ala
    50                  55                  60

Thr Ser Phe Gln Glu Arg Ala Ala Val Leu Arg Arg Ala Gly Asp Leu
65                  70                  75                  80

Trp Gln Gln His Ala Ala Glu Leu Lys Asp Trp Leu Ile Arg Glu Ser
                85                  90                  95

Gly Ser Ile Pro Gly Lys Ala Asp Phe Glu Leu His Val Ala Ala Gln
            100                 105                 110

Glu Cys Tyr Glu Ala Ala Ala Leu Pro Ser His Pro Thr Gly Glu Val
        115                 120                 125

Leu Pro Ser Glu Ala Pro Arg Leu Ser Met Ala Arg Arg Val Pro Ala
    130                 135                 140

Gly Val Val Gly Val Ile Ala Pro Phe Asn Ala Pro Leu Ile Leu Ser
145                 150                 155                 160
```

```
Ile Arg Ser Val Ala Pro Ala Leu Ala Leu Gly Asn Ser Val Val Leu
            165                 170                 175

Lys Pro Asp Pro Arg Thr Ala Val Cys Gly Gly Val Ala Leu Ala Arg
            180                 185                 190

Val Phe Glu Glu Ala Gly Leu Pro Ala Gly Val Leu His Val Leu Pro
            195                 200                 205

Gly Gly Pro Asp Val Gly Ala Ala Leu Val Glu Asp Lys His Val Arg
            210                 215                 220

Val Ile Ser Phe Thr Gly Ser Thr Ala Ala Gly Arg Ala Val Gly Glu
225                 230                 235                 240

Ser Ala Gly Arg His Leu Lys Arg Ala His Leu Glu Leu Gly Gly Asn
            245                 250                 255

Ser Ala Leu Ile Val Leu Asp Asp Ala Asp Leu Glu Gln Ala Met Ser
            260                 265                 270

Ala Ala Ala Trp Gly Ser Phe Phe His Gln Gly Gln Ile Cys Met Thr
            275                 280                 285

Thr Gly Arg His Leu Val His Ala Ser Leu Tyr Asp Glu Tyr Val Asp
            290                 295                 300

Arg Leu Ala Asp Lys Ala Ser His Leu Pro Val Gly Asn Pro Phe Thr
305                 310                 315                 320

Glu Gln Val Ala Leu Gly Pro Ile Ile Asp Ala Lys Gln Arg Asp Lys
            325                 330                 335

Ile His Gly Leu Val Thr Ser Ser Val Asp Ala Gly Ala Lys Val Ala
            340                 345                 350

Ala Gly Gly Thr Tyr Glu Asp Leu Phe Tyr Arg Ala Thr Val Leu Ala
            355                 360                 365

Gly Ala Gly Pro Ser Val Pro Ala Tyr Asp Gln Glu Val Phe Gly Pro
            370                 375                 380

Val Ala Pro Val Ala Lys Phe Thr Ser Leu Asp Glu Ala Ala Lys Leu
385                 390                 395                 400

Ala Ser Glu Ser Glu Tyr Gly Leu Ser Leu Gly Ile Ile Thr Ala Asp
            405                 410                 415

Val Ala Lys Gly Leu Ala Leu Ala Asp Arg Ile Pro Thr Gly Ile Ala
            420                 425                 430

His Ile Asn Asp Gln Thr Val Asn Asp Glu Ala Leu Ala Pro Phe Gly
            435                 440                 445

Gly Val Phe Asp Ser Gly Thr Gly Ser Arg Phe Gly Gly Pro Ala Ala
            450                 455                 460

Asn Ile Glu Ala Phe Thr Glu Thr Arg Trp Val Thr Met Arg Gly Asp
465                 470                 475                 480

Val Ala Gly Tyr Pro Phe
                485

<210> SEQ ID NO 2
<211> LENGTH: 171
<212> TYPE: PRT
<213> ORGANISM: Actinomycetales

<400> SEQUENCE: 2

Glu Ala Pro Met Ser Glu Thr Thr Pro Pro Ala Val Tyr Gln Gly Phe
1               5                   10                  15

Asp Arg Met Phe Leu Gly Gly Glu Trp Arg Ala Gly Ser Gly Gly Pro
            20                  25                  30

Leu Thr Asp Ser Asp Pro Tyr Thr Gly Asp Val Leu Thr Glu Ile Thr
        35                  40                  45
```

```
Pro Thr Gly His Gly Asp Val Asp Phe Ala Tyr Arg Ala Ala Leu Glu
    50                  55                  60

Ala Gln Arg Gly Trp Ser Ala Thr Pro Gly Glu Arg Ala Ala Val
65                  70                  75                  80

Phe Glu Arg Ala Thr Arg Ile Ile Gly Glu Arg Gln Ala Glu Ile Val
                85                  90                  95

Asp Trp Leu Val Arg Glu Ala Gly Ala Thr Leu Ala Arg Ala Ala Val
            100                 105                 110

Glu Val Gly Ile Val Gln Ala Val Thr Ala Ala Val Arg His Thr
            115                 120                 125

Glu Glu Val Val Val Thr Thr Asp Ser Asp Val Pro Asp Lys Glu Asn
130                 135                 140

Arg Val Tyr Arg Arg Pro Ala Gly Val Val Thr Val Ile Ser Pro Trp
145                 150                 155                 160

Trp Arg Pro Arg Trp His Trp Ala Thr Pro Ser
                165                 170

<210> SEQ ID NO 3
<211> LENGTH: 267
<212> TYPE: PRT
<213> ORGANISM: Actinomycetales

<400> SEQUENCE: 3

Arg Glu Gly Cys Ser Trp Pro Arg Ser Ser Lys Arg Pro Gly Ser Arg
1               5                   10                  15

Pro Gly Arg Gly Ile Ile Ala Lys Ala Gly Ile Lys Arg Leu Ser Leu
            20                  25                  30

Glu Leu Gly Gly Asn Gly Pro Leu Val Ile Leu Asp Asp Ala Asp Leu
        35                  40                  45

Glu Arg Ala Val Glu Cys Ala Val Phe Gly Ser Tyr Tyr His Gln Gly
    50                  55                  60

Gln Ile Cys Met Ala Thr Asn Arg Val Ile Val Asp Ala Ser Val His
65                  70                  75                  80

Asp Glu Phe Val Asp Arg Phe Val Glu Gln Ala Arg Ala Leu Arg Val
                85                  90                  95

Gly Asp Pro Arg Asp Pro Ala Thr Gln Ile Gly Pro Val Ile Ser Asp
            100                 105                 110

Arg Gln Leu Gly Thr Val Arg Asp Lys Ile Glu Arg Ala Val Ala Gly
        115                 120                 125

Gly Ala Arg Leu Leu Leu Ser Gly Glu Pro Thr Gly Pro Thr Gly Arg
    130                 135                 140

Val Leu Pro Pro His Val Leu Leu Gly Asp Asn His Val Ala Thr Ala
145                 150                 155                 160

Ala Glu Glu Val Phe Gly Pro Val Ala Thr Ile Ile Arg Ala Gln Asp
                165                 170                 175

Glu Glu Asp Ala Leu Arg Ile Ala Asn Asp Thr Asp Ala Gly Leu Ser
            180                 185                 190

Ser Gly Val Phe Thr Glu Asp Val Glu Arg Gly Leu Arg Phe Ala Leu
        195                 200                 205

Arg Val Glu Ala Gly Met Thr His Ile Asn Asp Thr Thr Val His Asp
    210                 215                 220

Asp Val His Ile Ala Phe Gly Gly Glu Lys Ala Ser Gly Leu Gly Arg
225                 230                 235                 240

Phe Gly Gly His Trp Val Ala Glu Glu Phe Thr Thr Gln His Trp Ile
```

```
                    245                 250                 255
Ser Ile Gln His Lys Pro Arg Asp Leu Ile Tyr
            260                 265

<210> SEQ ID NO 4
<211> LENGTH: 1461
<212> TYPE: DNA
<213> ORGANISM: Amycolatopsis sp. ATCC 39116

<400> SEQUENCE: 4
gtgagctttc tcgacgacga gaagtggacc ggacgcgtct tcaccggcag ctgggagcgc      60
gcggcgggcg gcgacgcggc cgtcatcgag cccgcgaccg cgacgaact  ggggcgcgtc     120 ggcatcgcct cgccccagga cctggcggcc tccgcggcca aggcggccga ggcgcagcgc     180
gcctgggcgg cgacctcctt caagaacgc  gccgcggtcc tgcgccgcgc cggcgacctg     240
tggcagcagc acgccgccga gctgaaggac tggctgatcc gcgagtcggg cagcatcccc     300
ggcaaggccg acttcgaact gcacgtcgcc gcgcaggagt gctacgaggc cgccgcgctg     360
ccctcccacc cgacgggtga ggtcctgccg agcgaggcgc cgcggctgag catggcccgc     420
cgcgtgcccg ccgcgtggt  cggcgtgatc gcgccgttca acgcgccgct gatcctgtcg     480
atccgctcgg tcgcgccggc gctggcgctg ggcaacagcg tcgtgctcaa gccggacccc     540
cgcaccgcgg tctgcggtgg cgtggcgctg gccagggtct tcgaggaggc cgggctgccc     600
gccggggtcc tgcacgtgct gccgggcggc ccggacgtcg gcgccgcgct ggtcgaggac     660
aagcacgtcc gcgtcatctc gttcaccgga tcgaccgccg cgggccgcgc ggtcggcgag     720
tccgcgggcc gccacctcaa gcgcgcccac ctggaactgg gcggcaactc ggcgctgatc     780
gtgctcgacg acgccgacct ggagcaggcg atgagcgccg ccgcgtgggg ctcgttcttc     840
caccagggcc agatctgcat gaccaccggg cggcacctgg tgcacgcctc actctacgac     900
gaatacgtgg accgcctggc ggacaaggcc agccacctgc cggtgggcaa cccgttcacc     960
gagcaggtcg cgctcggccc gatcatcgac gccaagcagc gcgacaagat ccacggcctg    1020
gtgacgtcca gtgtggacgc cggcgcgaag gtcgccgcgg gcggcaccta cgaggacctc    1080
ttctaccgcg ccaccgtgct cgccggcgcg ggcccctcgg tgcccgccta cgaccaggag    1140
gtgttcggcc cggtcgcccc ggtcgcgaag ttcaccagcc tggacgaggc cgcgaagctc    1200
gcgtcggaga gcgagtacgg gctgtcgctg ggcatcatca ccgcggacgt ggcgaaggga    1260
ctggcgctgg ccgaccgcat cccgaccggc atcgcgcaca tcaacgacca gacggtcaac    1320
gacgaggcgc tggccccgtt cggcggcgtg ttcgactccg cgaccggctc ccgcttcggc    1380
gggccggccg cgaacatcga ggcgttcacc gagacccgct gggtcacgat gcgcggcgac    1440
gtcgccggct acccgttctg a                                              1461

<210> SEQ ID NO 5
<211> LENGTH: 486
<212> TYPE: PRT
<213> ORGANISM: Amycolatopsis sp. ATCC 39116

<400> SEQUENCE: 5

Val Ser Phe Leu Asp Asp Glu Lys Trp Thr Gly Arg Val Phe Thr Gly
1               5                   10                  15

Ser Trp Glu Arg Ala Ala Gly Gly Asp Ala Ala Val Ile Glu Pro Ala
            20                  25                  30

Thr Gly Asp Glu Leu Gly Arg Val Gly Ile Ala Ser Pro Gln Asp Leu
        35                  40                  45
```

-continued

Ala Ala Ser Ala Ala Lys Ala Ala Glu Ala Gln Arg Ala Trp Ala Ala
        50              55              60

Thr Ser Phe Gln Glu Arg Ala Ala Val Leu Arg Ala Gly Asp Leu
65              70              75              80

Trp Gln Gln His Ala Ala Glu Leu Lys Asp Trp Leu Ile Arg Glu Ser
            85              90              95

Gly Ser Ile Pro Gly Lys Ala Asp Phe Glu Leu His Val Ala Ala Gln
            100             105             110

Glu Cys Tyr Glu Ala Ala Leu Pro Ser His Pro Thr Gly Glu Val
        115             120             125

Leu Pro Ser Glu Ala Pro Arg Leu Ser Met Ala Arg Arg Val Pro Ala
        130             135             140

Gly Val Gly Val Ile Ala Pro Phe Asn Ala Pro Leu Ile Leu Ser
145             150             155             160

Ile Arg Ser Val Ala Pro Ala Leu Ala Leu Gly Asn Ser Val Val Leu
            165             170             175

Lys Pro Asp Pro Arg Thr Ala Val Cys Gly Gly Val Ala Leu Ala Arg
            180             185             190

Val Phe Glu Glu Ala Gly Leu Pro Ala Gly Val Leu His Val Leu Pro
        195             200             205

Gly Gly Pro Asp Val Gly Ala Ala Leu Val Glu Asp Lys His Val Arg
        210             215             220

Val Ile Ser Phe Thr Gly Ser Thr Ala Ala Gly Arg Ala Val Gly Glu
225             230             235             240

Ser Ala Gly Arg His Leu Lys Arg Ala His Leu Glu Leu Gly Gly Asn
            245             250             255

Ser Ala Leu Ile Val Leu Asp Asp Ala Asp Leu Glu Gln Ala Met Ser
            260             265             270

Ala Ala Ala Trp Gly Ser Phe Phe His Gln Gly Gln Ile Cys Met Thr
        275             280             285

Thr Gly Arg His Leu Val His Ala Ser Leu Tyr Asp Glu Tyr Val Asp
        290             295             300

Arg Leu Ala Asp Lys Ala Ser His Leu Pro Val Gly Asn Pro Phe Thr
305             310             315             320

Glu Gln Val Ala Leu Gly Pro Ile Ile Asp Ala Lys Gln Arg Asp Lys
            325             330             335

Ile His Gly Leu Val Thr Ser Ser Val Asp Ala Gly Ala Lys Val Ala
            340             345             350

Ala Gly Gly Thr Tyr Glu Asp Leu Phe Tyr Arg Ala Thr Val Leu Ala
        355             360             365

Gly Ala Gly Pro Ser Val Pro Ala Tyr Asp Gln Glu Val Phe Gly Pro
        370             375             380

Val Ala Pro Val Ala Lys Phe Thr Ser Leu Asp Glu Ala Ala Lys Leu
385             390             395             400

Ala Ser Glu Ser Glu Tyr Gly Leu Ser Leu Gly Ile Ile Thr Ala Asp
            405             410             415

Val Ala Lys Gly Leu Ala Leu Ala Asp Arg Ile Pro Thr Gly Ile Ala
            420             425             430

His Ile Asn Asp Gln Thr Val Asn Asp Glu Ala Leu Ala Pro Phe Gly
        435             440             445

Gly Val Phe Asp Ser Gly Thr Gly Ser Arg Phe Gly Gly Pro Ala Ala
450             455             460

Asn Ile Glu Ala Phe Thr Glu Thr Arg Trp Val Thr Met Arg Gly Asp
465                 470                 475                 480

Val Ala Gly Tyr Pro Phe
            485

<210> SEQ ID NO 6
<211> LENGTH: 20
<212> TYPE: DNA
<213> ORGANISM: Artificial
<220> FEATURE:
<223> OTHER INFORMATION: T7 promoter primer

<400> SEQUENCE: 6
taatacgact cactataggg                                           20

<210> SEQ ID NO 7
<211> LENGTH: 19
<212> TYPE: DNA
<213> ORGANISM: Artificial
<220> FEATURE:
<223> OTHER INFORMATION: T7 terminator primer

<400> SEQUENCE: 7
gctagttatt gctcagcgg                                            19

<210> SEQ ID NO 8
<211> LENGTH: 29
<212> TYPE: DNA
<213> ORGANISM: Artificial
<220> FEATURE:
<223> OTHER INFORMATION: vdh_for_RBS_NdeI

<400> SEQUENCE: 8
aaaacatatg aaacctcgcg catcaggag                                 29

<210> SEQ ID NO 9
<211> LENGTH: 32
<212> TYPE: DNA
<213> ORGANISM: Artificial
<220> FEATURE:
<223> OTHER INFORMATION: vdh_rev_XhoI

<400> SEQUENCE: 9
aaaactcgag agaactggcg ctggtgcttc gt                             32

<210> SEQ ID NO 10
<211> LENGTH: 30
<212> TYPE: DNA
<213> ORGANISM: Artificial
<220> FEATURE:
<223> OTHER INFORMATION: vdh_rev_ohneStop_XhoI

<400> SEQUENCE: 10
aaaactcgag gaacgggtag ccggcgacgt                                30

<210> SEQ ID NO 11
<211> LENGTH: 24
<212> TYPE: DNA
<213> ORGANISM: Artificial
<220> FEATURE:
<223> OTHER INFORMATION: vdhLF_for3

<400> SEQUENCE: 11
tcgtacttcg cggtgatctc gtgg                                      24

```
<210> SEQ ID NO 12
<211> LENGTH: 27
<212> TYPE: DNA
<213> ORGANISM: Artificial
<220> FEATURE:
<223> OTHER INFORMATION: vdhLF_rev_KmR

<400> SEQUENCE: 12
gacgagttct tctgacgcgc ggcgggg                                      27

<210> SEQ ID NO 13
<211> LENGTH: 30
<212> TYPE: DNA
<213> ORGANISM: Artificial
<220> FEATURE:
<223> OTHER INFORMATION: vdhRF_for_PromKmR

<400> SEQUENCE: 13
ccagctggca attcctgtca ctcctgatgc                                   30

<210> SEQ ID NO 14
<211> LENGTH: 25
<212> TYPE: DNA
<213> ORGANISM: Artificial
<220> FEATURE:
<223> OTHER INFORMATION: vdhRF_rev3

<400> SEQUENCE: 14
ttgcagtcct ttgtagagcg acacg                                        25

<210> SEQ ID NO 15
<211> LENGTH: 30
<212> TYPE: DNA
<213> ORGANISM: Artificial
<220> FEATURE:
<223> OTHER INFORMATION: KmR_rev_vdhLF

<400> SEQUENCE: 15
cgcccccgcc gcgcgtcaga agaactcgtc                                   30

<210> SEQ ID NO 16
<211> LENGTH: 30
<212> TYPE: DNA
<213> ORGANISM: Artificial
<220> FEATURE:
<223> OTHER INFORMATION: PromKmR_for_vdhRF

<400> SEQUENCE: 16
gcatcaggag tgacaggaat tgccagctgg                                   30
```

MICROORGANISMS AND METHODS FOR PRODUCING SUBSTITUTED PHENOLS

CROSS-REFERENCE TO RELATED APPLICATIONS

This application is National Stage of International Application No. PCT/EP2012/061600, filed 18 Jun. 2012, which claims the benefit under 35 U.S.C. §119(e) of U.S. Provisional Application No. 61/498,223, filed 17 Jun. 2011, and which claims the benefit under 35 U.S.C. §119(a)-(d) and (f) of EP 11170461.5, filed 17 Jun. 2011, each of which incorporated by reference in its entirety.

The present invention is concerned with methods for producing vanillin, feruloyl-CoA, ferulic acid, coniferyl aldehyde and/or coniferyl alcohol. Also, the invention relates to microorganisms useful in such production methods, and to the construction of such microorganisms.

Vanillin is one of the major aroma substances of economic importance. However, vanillin is difficult to obtain from natural sources or by natural processes, i.e. by physical processes including distillation and extraction, enzymatic or microbiological treatment of educts, wherein the educts are of plant or animal origin used as such or used in a form processed by conventional food technology including drying, roasting and fermentation.

One of the major natural sources is vanilla plant material. However, growing, harvesting and processing such vanilla plant material is costly. It has therefore been tried to produce natural vanillin using other sources than vanilla plant material.

EP 761 817 A2 discloses a method of producing vanillin from ferulic acid using microorganisms of family pseudonocardia. However, ferulic acid is a costly educt on its own. The process described in this publication thus does not mitigate the above problem sufficiently. The publication discusses production of ferulic acid from eugenol by using microorganisms of genus *Pseudomonas*, so as to achieve a conversion of eugenol to vanillin in a two-step process. However, such two-step processes are difficult to handle and entail unwanted additional costs compared to a one-step process.

Overhage et al. (Appl. Env. Microbiol., 69 (2003), 6569-6576) disclose a highly efficient biotransformation of eugenol to ferulic acid and further conversion to vanillin in recombinant strains of *E. coli*. However, yields of vanillin were too low for an economically feasible process.

Overhage et al. (J. Biotechnol. 125 (2006), 369-376) further describe a recombinant strain of genus *Amycolatopsis* for producing vanillin from eugenol in a one-step process. However, the strain accumulated significant amounts of intermediates of the conversion process and only provided a low yield of vanillin.

It was thus the problem of the present invention to provide a method for producing a product selected from vanillin, feruloyl-CoA, ferulic acid, coniferyl aldehyde and coniferyl alcohol, and preferably of vanillin, by conversion of an educt selected from eugenol, coniferyl alcohol, coniferyl aldehyde and ferulic acid, avoiding or reducing the above drawbacks of the prior art. The problem also pertains to providing one or more microorganisms useful in such production method, and also pertains to the construction of such microorganisms.

According to the invention there is thus provided a method for producing a product selected from vanillin, feruloyl-CoA, ferulic acid, coniferyl aldehyde and coniferyl alcohol, comprising the step of adding an educt selected from eugenol, coniferyl alcohol, coniferyl aldehyde and ferulic acid to a microorganism of order Actinomycetales, preferably of genus *Amycolatopsis* or genus *Streptomyces*, wherein the microorganism does not comprise a gene coding for a vanillin dehydrogenase.

It has now been found that a major obstacle to an economically feasible use of microorganisms of the Actinomycetales order is the presence of a gene coding for a vanillin dehydrogenase. Such enzyme catalyzes the conversion of vanillin to vanillic acid, thereby reducing the yield of vanillin. Also, it has now been found that in the Actinomycetales order, and specifically in genus *Amycolatopsis*, it is sufficient to inactivate or delete one vanillin dehydrogenase gene to prevent or significantly reduce the conversion rate of vanillin to vanillic acid in vivo.

It was known from WO 00/26355 A2 that in *Pseudomonas* sp. DSMZ 7063, which is able to convert eugenol to vanillin, a vanillin dehydrogenase gene exists which can be inactivated to increase the yield of vanillin. However, genus *Pseudomonas* and the Actinomycetales order and particularly genus *Amycolatopsis* are taxonomically very distant from each other, and are separated by the taxonomic ranks of phylum, class and order. Thus it could not be expected that members of the Actinomycetales would comprise only one gene coding for a vanillin dehydrogenase, or that inactivation or deletion of a vanillin dehydrogenase gene or gene product would be sufficient to significantly increase vanillin yield. Also, Achterholt et al. (Appl. Microbiol. Biotechnol 54 (2000), 799-807) describe a putative metabolic pathway for the conversion of ferulic acid to guaiacol. The authors describe that vanillin can be converted to vanillic acid, and also feruloyl-CoA, an intermediate for the production of vanillin, can be converted to vanillic acid via vanillyl-CoA. It was therefore to be expected that even if the direct conversion of vanillin to vanillic acid could be inhibited, vanillic acid would still be produced in significant amounts due to the vanillyl-CoA shunt, thereby still reducing vanillin yields.

Accordingly, the invention also provides a microorganism of order Actinomycetales, preferably of genus *Amycolatopsis* or genus *Streptomyces*, wherein the microorganism does not comprise a gene coding for a vanillin dehydrogenase. Such microorganism is particularly suitable for producing a product selected from vanillin, feruloyl-CoA, ferulic acid, coniferyl aldehyde and coniferyl alcohol in the above method according to the present invention, and preferably for producing vanillin. Methods and means for producing such microorganism are also described hereinafter according to the invention.

The microorganism, and correspondingly the method according to the present invention, allows to produce

- vanillin from any of eugenol, coniferyl alcohol, coniferyl aldehyde, ferulic acid and feruloyl-CoA
- feruloyl-CoA from any of eugenol, coniferyl alcohol, coniferyl aldehyde and ferulic acid,
- ferulic acid from any of eugenol, coniferyl alcohol and coniferyl aldehyde
- coniferyl aldehyde from any of eugenol and coniferyl alcohol, or
- coniferyl alcohol from eugenol.

Preferred according to the invention are methods and microorganisms for the production of vanillin from ferulic acid or eugenol. Most preferred according to the present invention are methods and microorganisms for the production of vanillin from eugenol.

BRIEF DESCRIPTION OF THE FIGURES

FIG. 2 shows the nucleotide sequence of the vdh gene of *Amycolatopsis* sp. ATCC 39116 (SEQ ID NO: 4).

FIG. 3 shows the amino acid sequence of vanillin dehydrogenase (VDH) of *Amycolatopsis* sp. ATCC 39116 (SEQ ID NO: 5).

Figure 1:
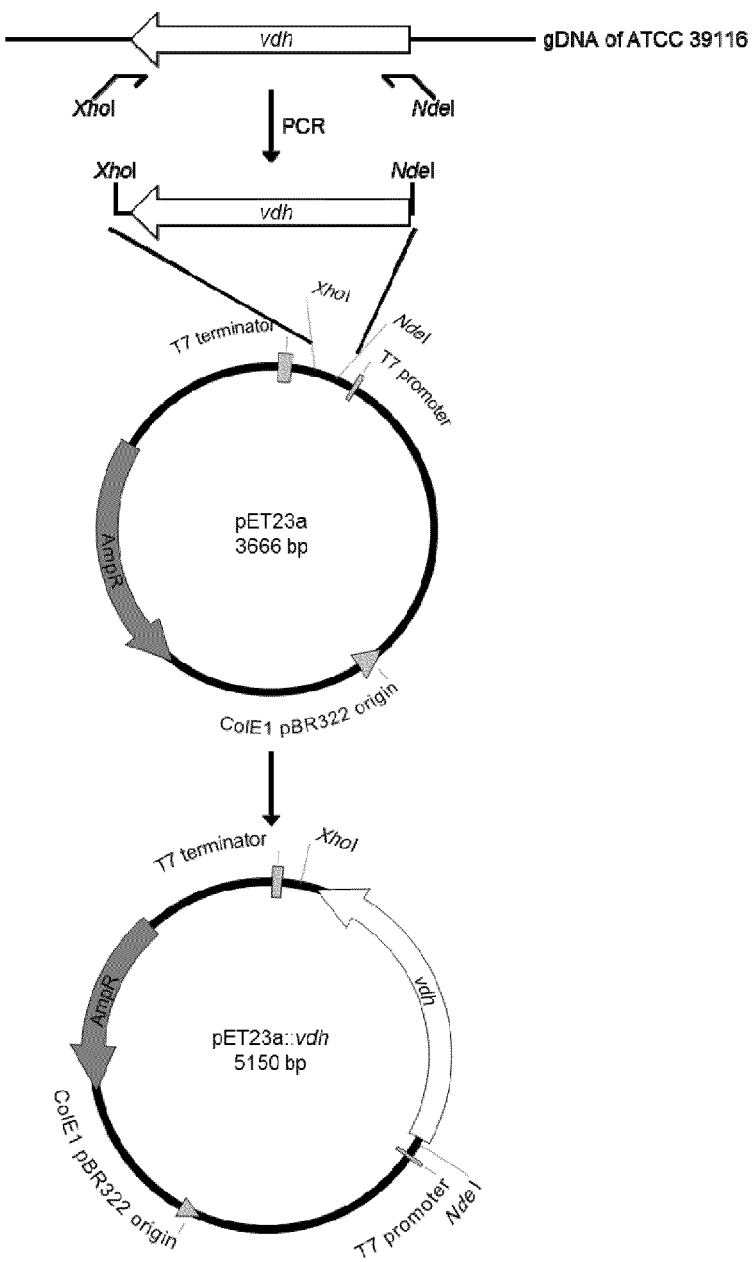
FIG. 1 shows the construction of the pET23a::vdh hybrid plasmid.

In the method of production according to the present invention, the microorganism of the present invention is exposed to a selected educt under conditions allowing to produce the selected product. Such conditions are described, for example, in EP 761 817 A2 for the production of vanillin from ferulic acid. For the purposes of the present invention, EP 761 817 A2 is incorporated into the present description in its entirety. The desired product can be obtained by any suitable purification method. The skilled person may choose such purification method for example based on the description of H. Chmiel in Chmiel et al., BioprozeRtechnik 2, G. Fischer Verlag 1991, ISBN 3-437-20480-7.

The microorganism of the present invention, which can be used in the method of the present invention, belongs to the family of Actinomycetales, preferably to a suborder selected from the group consisting of Actinomycineae, Actinopolysporineae, Catenulisporineae, Corynebacterineae, Frankineae, Glycomycineae, Kineosporiineae, Micrococcineae, Micromonosporineae, Propionibacterineae, Pseudonocardineae, Streptomycineae and Streptosporanginea, wherein the suborders of Pseudonocardineae and Streptomycineae are preferred, and even more preferably belongs to the family of Pseudonocardiaceae or Streptomycetaceae, and even more preferably to genus *Amycolatopsis* or *Streptomyces*, and most preferably to genus *Amycolatopsis*.

Among genus *Amycolatopsis*, the strains *Amycolatopsis* sp. ATCC 39116, HR 167 and DSMZ 9992, respectively, are particularly preferred in connection with the present invention. These strains exhibit a very high vanillin tolerance and allow achieving good yields of vanillin by conversion of ferulic acid even prior to the inactivation or deletion of the vanillin dehydrogenase gene according to the present invention.

The vanillin dehydrogenase according to the invention preferably has an amino acid sequence according to any of SEQ ID NOs: 1, 2 or 3, or an amino acid sequence having a sequence similarity of at least 90% to an amino acid sequence according to any of SEQ ID NOs: 1, 2 or 3. According to the present invention, similarity of amino acid sequences is determined using the EMBOSS:water-program (Algorithm of Smith and Waterman (1981), Identification of common molecular subsequences, J. Mol. Biol. 147:195-197), wherein the parameters are: Gap open penalty: 10.0; Gap extension penalty: 0.5; Blosum62-Matrix. The program calculates a "similarity" percentage value, which is the similarity percentage value according to the present invention. Correspondingly, the similarity of nucleic acid sequences is determined using the EMBOSS:water-program (Algorithm of Smith and Waterman (1981), Identification of common molecular subsequences, J. Mol. Biol. 147:195-197), wherein the parameters are: Gap open penalty: 10.0, Gap extension penalty: 0.5; DNAfull matrix. The EMBOSS: water program is available online via the EBI at ebi.ac.uk/Tools/psa/.

It has now been found that in microorganisms of order Actinomycetales, and particularly of genus *Amycolatopsis*, even more particularly in *Amycolatopsis* sp. ATCC 39116, one gene for a vanillin dehydrogenase as defined above is naturally present. Inactivation or deletion of this gene allows the increase the yield of vanillin obtainable by conversion of, for example, eugenol and/or ferulic acid.

The gene coding for a vanillin dehydrogenase according to the present invention is preferably inactivated or deleted in the microorganism of the present invention. Thus, a microorganism of the present invention is preferred wherein the microorganism comprises a) a vanillin dehydrogenase gene inactivated by an insert or a deletion, and/or b) a left and a right flanking region, each having a length of 50-1500 nucleotides and a sequence similarity of at least 95% to a sequence of identical length within 2000 nucleotides to the left and right, respectively, of an *Amycolatopsis* or *Streptomyces* wild type vanillin dehydrogenase gene, wherein the nucleic acid sequence between the left and right flanking region does not comprise a gene coding for a vanillin dehydrogenase.

According to option a), the vanillin dehydrogenase gene is inactivated by an insert or a deletion. Such insert or deletion can be accomplished by any suitable means. For example, the reading frame of the gene could be disrupted such that if the nucleic acid of the gene is transcribed and translated, the resulting protein could not catalyze the reaction of vanillin to vanillic acid. The insertion or deletion could also result in the shortening of the resulting protein, e.g. by deletion of one or more codons or by insertion of a stop codon, such that after transcription and translation a protein would be obtained that does not catalyze the reaction of vanillin to vanillic acid. Also, the vanillin dehydrogenase gene may be inactivated by insertion of additional nucleotides to introduce additional amino acids into the amino acid sequence of vanillin dehydrogenase to prevent the resulting protein from folding correctly. Again, the resulting protein would be unable to catalyze the reaction of vanillin to vanillic acid. The insertion or deletion could also be made in or span a transcription regulatory site, for example a promoter region, of the vanillin dehydrogenase gene, such the gene will not be or only at a significantly reduced rate transcribed and translated, compared to the corresponding wildtype microorganism. Insertions and deletions may also be coupled to replace one or more nucleotides, thereby altering the amino acid sequence of a protein which would be obtainable by transcription and translation of the gene, or preventing the gene from being transcribed or translated at all. Replacements, i.e. simultaneous insertions and deletions, may be introduced using an omega element.

Particularly preferred aspects of methods and microorganisms according to the present invention can be derived from the examples described herein below (see e.g. example 5).

According to option b), the gene for vanillin dehydrogenase is replaced by an omega element to introduce a nucleic acid segment which does not comprise a gene coding for a vanillin dehydrogenase. The introduced nucleic acid segment may preferably comprise a selection marker, preferably a gene coding for a gene conferring resistance against an antimicrobial agent, for example resistance against tetracyclin, kanamycin or chloramphenicol. The gene may be under the control of a constitutive or inducible promoter. The construction of omega elements is described in WO 00/26355 A2 for vanillin dehydrogenase of *Pseudomonas* sp. HR199; the methods described therein can be adopted accordingly to construct omega elements to replace the vanillin dehydrogenase gene in microorganisms of the present invention. Other omega elements and methods of their construction are described in Alexeyev et al. (Gene 160 (1995), 63-67).

To further increase the yield of vanillin or other desired products, the microorganism of the present invention optionally further comprises any of a) an eugenol hydroxylase gene of *Pseudomonas* sp. DSMZ 7063, a vanillyl alcohol oxidase gene of *Penicillium simplicissimium*, an eugenol oxidase gene of *Rhodococcus jostii* RHA1, b) a coniferyl alcohol dehydrogenase gene of *Pseudomonas* sp. DSMZ 7063, an aromatic alcohol dehydrogenase gene (adhA; accession number AB213394) of *Rhodococcus opacus* TKN14, an aryl alcohol dehydrogenase gene of *Acinetobacter* sp. ADP1, an aryl alcohol dehydrogenase gene of *Rhodococcus erythropolis* PR4, *Lactobacillus plantarum* WCFS1 (lp_3054; accession number CAB69495) and *Gordonia polyisoprenivorans* Kd2 (adhA, accession number ZP_09272609.1), c) a coniferyl aldehyde dehydrogenase of *Pseudomonas* sp. DSMZ 7063, a benzaldehyd dehydrogenase of *Acinetobacter* sp. ADP1, a aldehyd-dehydrogenase of *Arabidopsis thaliana* (ALDH2C4, accession number NM_113359.3), a benzaldehyd dehydrogenase of *Pseudomonas putida* mt-2 (XylC, accession number U15151.1), a dodecanal dehydrogenase *Gluconobacter oxydans* 521H (accession number YP_190934), d) a feruloyl-CoA-synthetase of *Pseudomonas* sp. DSMZ 7063, e) an enoyl-CoA-hydratase/aldolase of *Pseudomonas* sp. DSMZ 7063, or a gene coding for an enzyme having a sequence similarity of at least 95% to the sequence of any of the aforementioned genes.

According to option a), the additional enzyme improves catalysis of the conversion of eugenol to coniferyl alcohol. Such genes and methods thereof are described for example in Overhage et al. (Appl. Env. Microbiol., 69 (2003), 6569-6576), Overhage et al. (J. Biotechnol. 125 (2006), 369-376) and Priefert et al. (Appl. Microbiol. Biotechnol. 56 (2001), 296-314).

According to option b), the additional enzyme improves catalysis of the conversion of coniferyl alcohol to coniferyl aldehyde. Such genes and methods thereof are described for example in Overhage et al. (Appl. Env. Microbiol., 69 (2003), 6569-6576) and Overhage et al. (J. Biotechnol. 125 (2006), 369-376).

According to option c), the additional enzyme improves catalysis of the conversion of coniferyl aldehyde to ferulic acid. Such genes and methods thereof are described for example in Overhage et al. (Appl. Env. Microbiol., 69 (2003), 6569-6576) and Overhage et al. (J. Biotechnol. 125 (2006).

According to option d), the additional enzyme improves catalysis of the conversion of ferulic acid to feruloyl-CoA. Such genes and methods thereof are described for example in Overhage et al. (Appl. Env. Microbiol., 65 (1999), 4837-4847).

According to option e), the additional enzyme improves catalysis of the conversion of feruloyl-CoA to vanillin. Such genes and methods thereof are described for example in Overhage et al. (Appl. Env. Microbiol., 65 (1999), 4837-4847).

The additional gene or genes coding for any of the above enzymes improve the production of vanillin by providing additional metabolic means for converting the respective educt to the corresponding product, thereby increasing the amount of enzymes to catalyze the respective reaction.

Particularly preferred microorganisms of the present invention are of genus *Amycolatopsis*, even more preferred of strain *Amycolatopsis* sp. ATCC 39116, wherein the gene for vanillin dehydrogenase is inactivated by an insertion of an antibiotic resistance gene into the gene coding for vanillin dehydrogenase. Another preferred option is the generation of a markerless vanillin dehydrogenase knockout mutant. Further preferred are those microorganisms of the present invention which additionally comprise one or more genes according to above options a), b) and/or c).

Thus, a particularly preferred microorganism is of genus *Amycolatopsis* or of *Amycolatopsis* sp. ATCC 39116, with the following modifications:
  the gene for vanillin dehydrogenase is inactivated by an insertion of an antibiotic resistance gene into the gene coding for vanillin dehydrogenase; and
  the microorganism additionally comprises a vanillyl alcohol oxidase gene of *Penicillium simplicissimium* and/or an eugenol oxidase gene of *Rhodococcus jostii* RHA1;
  preferably the microorganism additionally comprises a coniferyl alcohol dehydrogenase gene of *Pseudomonas* sp. DSMZ 7063 and a coniferyl aldehyde dehydrogenase of *Pseudomonas* sp. DSMZ 7063.

Such microorganism is able to convert eugenol to vanillin at very high yields, and is thus preferred in a corresponding method of the present invention.

Particularly preferred are microorganisms comprising one or more of the aforementioned additional enzymes or, respectively, one or more of the corresponding genes (as described above).

The present invention also provides methods for constructing a microorganism of the present invention, comprising the steps of:
i) providing a microorganism of order Actinomycetales, preferably of genus *Amycolatopsis* or genus *Streptomyces*,
ii) transforming the microorganism with an omega element to inactivate a gene coding for a vanillin dehydrogenase,
iii) selecting a recombinant obtained by the transformation of step ii).

As described above, such omega elements are particularly useful to in inactivate a gene coding for vanillin dehydrogenase. Particularly, such omega elements do not disrupt the organization of further genes of the microorganism.

A further preferred construction method according to the present invention comprises the additional steps of iv) before or after step ii) or iii) transforming a microorganism with a vector comprising
   a) an eugenol hydroxylase gene of *Pseudomonas* sp. DSMZ 7063, a vanillyl alcohol oxidase gene of *Penicillium simplicissimium*, an eugenol oxidase gene of *Rhodococcus jostii* RHA1,
   b) a coniferyl alcohol dehydrogenase gene of *Pseudomonas* sp. DSMZ 7063, a aromatic alcohol dehydrogenase gene (adhA; accession number AB213394) of *Rhodococcus opacus* TKN14, a aryl alcohol dehydrogenase gene of *Acinetobacter* sp. ADP1, an aryl alcohol dehydrogenase gene of *Rhodococcus erythropolis* PR4, *Lactobacillus plantarum* WCFS1 (Ip_3054; accession number CAB69495) and *Gordonia polyisoprenivorans* Kd2 (adhA, accession number ZP_09272609.1),
   c) a coniferyl aldehyde dehydrogenase of *Pseudomonas* sp. DSMZ 7063, a benzaldehyd dehydrogenase of *Acinetobacter* sp. ADP1, a aldehyd-dehydrogenase of *Arabidopsis thaliana* (ALDH2C4, accession number NM_113359.3), a benzaldehyd dehydrogenase of *Pseudomonas putida* mt-2 (XylC, accession number U15151.1), a dodecanal dehydrogenase *Gluconobacter oxydans* 521H (accession number YP_190934),
   d) a feruloyl-CoA-synthetase of *Pseudomonas* sp. DSMZ 7063,
   e) an enoyl-CoA-hydratase/aldolase of *Pseudomonas* sp. DSMZ 7063,
   or a gene coding for an enzyme having a sequence similarity of at least 95% to the sequence of any of the aforementioned genes; and
v) selecting a microorganism comprising the respective gene(s) according to respective option(s) a)-e) of step iv).

Transformation of microorgansisms of order Actinomycetales, specifically of genus *Amycolatopsis*, has been described in Overhage et al. (J. Biotechnol. 125 (2006), 369-376); the methods described therein are used in the preferred construction method of the present invention, wherein the gene(s) to be transferred are those as defined in said options a)-e). Such method can be performed within reasonable time and costs.

The invention also provides a vanillin dehydrogenase gene, i.e. a gene coding for an enzyme for the conversion of vanillin to vanillic acid. According to the invention, such vanillin dehydrogenase can be used to catalyze the conversion of vanillin to vanillic acid. The invention therefore also provides a microorganism comprising said vanillin dehydrogenase as a heterologous gene or under the control of an inducible or repressible promoter, thereby allowing a biotechnological conversion of vanillin to vanillic acid. As described above, the vanillin dehydrogenase has an amino acid sequence according to any of SEQ ID NOs: 1, 2 or 3, or an amino acid sequence having a sequence similarity of at least 90% to an amino acid sequence according to any of SEQ ID NOs: 1, 2 or 3.

The invention is further described hereinafter by reference to examples and figures.

These examples and figures are not intended to limit the scope of disclosure or the scope of protection conferred by the attached patent claims.

1. MATERIAL AND METHODS

1. Strains and Plasmids

Unless described otherwise, the examples were performed using the bacterial strains described in table 1, the plasmids and hybrid plasmids of table 2 and the oligonucleotides of table 3 and using the methods described herein below.

TABLE 1

Bacterial strains

| bacterial strain | description | source |
| --- | --- | --- |
| *Amycolatopsis* sp. ATCC 39116 | wild type | Symrise (Holzminden, Germany) |
| *Amycolatopsis* sp. ATCC 39116 Δvdh::KmR | vdh-deletion mutant with a kanamycin resistance marker (KmR) instead of the vdh gene | present invention |
| *E. coli* Mach1 | F$^-$φ80(lacZ)ΔM15 ΔlacX74hsdR ($r_K^-$ $m_K^+$)ΔrecA1398 endA1 tonA | Invitrogen (Karlsruhe, Germany) |
| *E. coli* BL21(DE3) | F$^-$ompT hsdS$_B$($r_B^-$ $m_B^-$) gal dcm (DE3) | Novagen (Darmstadt, Germany) |
| *E. coli* BL21(DE3) (pET23a) | F$^-$ompT hsdS$_B$($r_B^-$ $m_B^-$) gal dcm (DE3) (Amp$^R$) | present invention |
| *E. coli* BL21(DE3) (pET23a::vdh) | F$^-$ompT hsdS$_B$($r_B^-$ $m_B^-$) gal dcm (DE3) (Amp$^R$) vdh$_{ATCC\ 39116}$ coding for VDH | present invention |
| *E. coli* BL21(DE3) (pET23a::vdhHis) | F$^-$ompT hsdS$_B$($r_B^-$ $m_B^-$) gal dcm (DE3) (Amp$^R$) vdh$_{ATCC\ 39116}$ coding for VDH with His$_6$-tag | present invention |
| *E. coli* Rosetta-gami B(DE3) pLysS | F$^-$ompT hsdS$_B$($r_B^-$ $m_B^-$) gal dcm lacY1 ahpC (DE3) gor522::Tn10trxB pLysSRARE (Cm$^R$, Km$^R$, Tet$^R$) | Novagen (Darmstadt, Germany) |
| *E. coli* Rosetta-gami B(DE3) pLysS (pET23a::vdh) | F$^-$ompT hsdS$_B$($r_B^-$ $m_B^-$) gal dcm lacY1 ahpC (DE3) gor522::Tn10trxB pLysSRARE (Amp$^R$, Cm$^R$, Km$^R$, Tet$^R$) vdh$_{ATCC\ 39116}$ coding for VDH | present invention |
| *E. coli* Rosetta 2 (DE3) pLysS | F$^-$ompT hsdS$_B$($r_B^-$ $m_B^-$) gal dcm (DE3) pLysSRARE2$^6$ (Cm$^R$) | Novagen (Darmstadt, Germany) |
| *E. coli* Rosetta 2 (DE3) pLysS (pET23a::vdh) | F$^-$ompT hsdS$_B$($r_B^-$ $m_B^-$) gal dcm (DE3) pLysSRARE2$^6$ (Amp$^R$, Cm$^R$) vdh$_{ATCC\ 39116}$ coding for VDH | present invention |
| *E. coli* HMS174(DE3) | F$^-$recA1 hsdR($r_{K12}^-$ $m_{K12}^+$) (DE3) (Rif$^R$) | Novagen (Darmstadt, Germany) |

TABLE 1-continued

Bacterial strains

| bacterial strain | description | source |
|---|---|---|
| E. coli HMS174(DE3) (pET23a::vdh) | F⁻recA1 hsdR($r_{K12}^-$ $m_{K12}^+$) (DE3) ($Amp^R$, $Rif^R$) $vdh_{ATCC\ 39116}$ coding for VDH | present invention |

TABLE 2

Plasmids and hybrid plasmids

| (hybrid) plasmid | description | source |
|---|---|---|
| pET23a | $Amp^R$, T7 promoter | Novagen (Darmstadt, Germany) |
| pET23a::vdh | $vdh_{ATCC\ 39116}$ coding for VDH cloned in NdeI and XhoI of pET23a colinear to T7 promoter | present invention |
| pET23a::vdhHis | $vdh_{ATCC\ 39116}$ coding for VDH with $His_6$-tag cloned in NdeI and XhoI of pET23a colinear to T7 promoter | present invention |

TABLE 3

Oligonucleotides

| oligonucleotide | nucleotide sequence (5'-3') | SEQ ID NO: |
|---|---|---|
| T7 promoter primer | TAATACGACTCACTATAGGG | 6 |
| T7 terminator primer | GCTAGTTATTGCTCAGCGG | 7 |
| vdh_for_RBS_NdeI | AAAAcatatgAAACCTCGCGCATCAGGAG | 8 |
| vdh_rev_XhoI | AAAActcgagAGAACTGGCGCTGGTGCTTCGT | 9 |
| vdh_rev_ohneStop_XhoI | AAAActcgagGAACGGGTAGCCGGCGACGT | 10 |
| vdhLF_for3 | TCGTACTTCGCGGTGATCTCGTGG | 11 |
| vdhLF_rev_KmR | GACGAGTTCTTCTGACGCGCGGCGGGG | 12 |
| vdhRF_for_PromKmR | CCAGCTGGCAATTCCTGTCACTCCTGATGC | 13 |
| vdhRF_rev3 | TTGCAGTCCTTTGTAGAGCGACACG | 14 |
| KmR_rev_vdhLF | CGCCCCGCCGCGCGTCAGAAGAACTCGTC | 15 |
| PromKmR_for_vdhRF | GCATCAGGAGTGACAGGAATTGCCAGCTGG | 16 |

Lower case letters indicate new restriction sites. Underlining indicates the ribosome binding site.

2. Growth Conditions for Bacteria

*Escherichia coli* was grown in liquid culture at 30° C. and 100 rpm on a rotary shaker in plain Erlenmeyer flasks. *E. coli* was cultured according to manufacturer's instructions in lysogeny broth (LB; Sambrook and Russell 2001), mineral salt medium (MSM; Schlegel et al. 1961) with added vitamins and a TEL solution according to Kroll et al. (2011) or HR-medium (Rabenhorst 1996). *Amycolatopsis* sp. ATCC 39116 was cultivated at 42° C. and 150 rpm in Tryptic soy broth (TSB; Merck, Darmstadt, Germany).

Solid media were prepared by addition of agar to a final concentration of 1.7% (w/v). Vanillin and vanillic acid were dissolved in dimethyl sulfoxide (DMSO) and were used in a final concentration of 14 mM.

For stabilization of plasmids or selection of bacterial strains antibiotics were added to the bacterial cultures as follows: ampicillin (Amp; 100 µg/ml), chloramphenicol (Cm; 34 µg/ml), kanamycin (Km; 15 µg/ml; 100 µg/ml for *Amycolatopsis* sp.), rifampicin (Rif; 200 µg/ml); tetracycline (Tet; 12.5 µg/ml).

Growth of bacteria was followed via determination of optical densities (OD) at 400 nm (*Amycolatopsis* sp. ATCC 39116) and 600 nm (*E. coli*), respectively.

3. Quantitative and Qualitative Determination of Metabolic Intermediates in Culture Supernatants Metabolic intermediates were analyzed using high performance liquid chromatography (HPLC; Dionex, Idstein, Germany). All substances were separated using a reversed-phase Nucleosil-100 C18 column and an acetonitrile-formic acid gradient (cf. Table 4) at a flow rate of 1 ml/min. Eluted compounds were identified using a multi-wavelength detector (MWD; Dionex, Idstein, Germany) based on their absorption spectra at 259 nm (vanillic acid) and 340 nm (vanillin), respectively, and on their respective retention time. If required culture supernatants were diluted with distilled water. Quantification was performed using calibrated standards.

TABLE 4

Acetonitrile-formate gradients for HPLC analysis

| | gradient composition [vol %] | |
|---|---|---|
| time [min:sec] | 0.1% (v/v) formic acid | acetonitrile |
| 0:00 | 74 | 26 |
| 6:30 | 74 | 26 |

TABLE 4-continued

Acetonitrile-formate gradients for HPLC analysis

| time [min:sec] | gradient composition [vol %] | |
|---|---|---|
| | 0.1% (v/v) formic acid | acetonitrile |
| 8:00 | 0 | 100 |
| 12:00 | 0 | 100 |
| 13:00 | 74 | 26 |
| 18:00 | 74 | 26 |

4. Obtaining a Soluble Fraction of Crude Extracts

Cells were harvested by centrifugation at 4000×g and 4° C. for 15 min in a laboratory centrifuge (Megafuge1.0 R, Heraeus, Osterode, Germany). After harvesting and washing of the resulting cell pellet in 100 mM potassium phosphate buffer (pH 7.0) cells were disrupted by a three-fold French press passage at 120 MPa (Aminco, Silver Spring, Md., USA). The soluble fraction was obtained by centrifugation at 20000×g and 4° C. for 30-60 min and stored on ice until further use or was aliquoted and frozen at −20° C.

5. Purification of Vanillin Dehydrogenase

The gene product of heterologously expressed $vdh_{ATCC\ 39116}$ was purified using a C-terminal-fused $His_6$-tag at 4° C. Cells were disrupted in binding buffer (20 mM sodium phosphate, 500 mM sodium chloride, 20 mM imidazole, pH 7.4). After equilibration of a "H is SpinTrap-column" (GE Healthcare, Freiburg, Germany) using 600 μl binding buffer the soluble fraction was added to the column. The column was washed six times using 600 μl washing buffer (20 mM sodium phosphate, 500 mM sodium chloride, 40 or 80 mM imidazole, pH 7.4), wherein the washing buffer contained 40 mM imidazole in the first three washing steps and 80 mM imidazole in the further three washing steps. Bound protein was eluted by addition of 200 μl elution buffer (20 mM sodium phosphate, 500 mM sodium chloride, 500 mM imidazole, pH 7.4). This step was repeated and the combined eluate was rebuffered in potassium phosphate buffer (pH 7.1) using "Vivaspin 500" (Sartorius stedim biotech, Goettingen, Germany) with 10 kDa molecular weight cutoff.

6. Determination of Vanillin Dehydrogenase Activity

Activity of vanillin dehydrogenase (VDH) in crude extract, in the soluble fraction or in the rebuffered eluate was done photometrically as described by Gasson et al. (1998). The reaction set contained in a volume of 1 ml 0.1 mmol potassium phosphate buffer (pH 7.1), 0.065 μmol vanillin, 0.5 μmol $NAD^+$, 1.2 μmol pyruvate (sodium salt), lactate dehydrogenase (LDH from rabbit muscle, 1 U) and enzyme solution (500 μg total protein). Oxidation of vanillin was monitored at 30° C. and a wavelength of λ=340 nm ($_{vanillin}$=11.6 $cm^2$/μmol). Enzyme activity was given in units (U), wherein 1 U corresponds to the amount of enzyme required for conversion of 1 μmol vanillin per minute. Protein concentration was determined according to Bradford (1976).

7. Electrophoretic Methods

Discontinuous sodium dodecyl sulfate-polyacrylamide gel electrophoresis (SDS-PAGE; 4.5% (w/v) stacking gel, 12.5% (w/v) resolving gel) was performed under denaturing conditions as described by Laemmli (1970). Polyacrylamide gels were stained with Serva Blue G.

8. Isolation, Manipulation and Transfer of DNA

Total DNA (gDNA) was isolated according to the manufacturer's instructions for Gram-positive bacteria using a "DNeasy Blood and Tissue Kit" (Qiagen, Hilden, Germany). Cells were lysed prior to isolation in lysis buffer having 20 mg/ml lysozyme and incubated at 37° C. for 60 min. Highly purified plasmid DNA was isolated from *E. coli* using "peqGOLD Plasmid Miniprep Kit" (PEQLAB Biotechnologie, Erlangen, Germany) according to the manufacturer's instructions. Competent *E. coli*-cells were prepared according to Hanahan (1983).

9. Determination of DNA Sequences

Sequencing of vectors was done using the BigDye® Terminator v3.1 Cycle Sequencing Kit (Applied Biosystems, Darmstadt, Germany):
BigDye® 2 μl
BigDye® buffer 2 μl
Plasmid with insert (1:5 diluted in distilled water) 4.5 μl
Oligonucleotide (10 mM) 1.5 μl

2. SPECIFIC EXAMPLES AND RESULTS

Example 1

Cloning of a Gene for Vanillin Dehydrogenase (VDH) of *Amycolatopsis* sp. ATCC 39116

First, hybrid plasmids
pET23a::vdh (cloning scheme cf. FIG. 1 (construction of the pET23a::vdh hybrid plasmid); Elements for plasmid replication of pET23a in *E. coli* are: the origin of replication ColE1 of pBR322 and the gene for β-lactamase. The IPTG inducible T7 promoter system consists of a T7 promoter, a T7 origin of transcription and a T7 terminator; the vdh gene was amplified using specific oligonucleotides on gDNA of *Amycolatopsis* sp. ATCC 39116 and was ligated into the NdeI and XhoI restriction sites of pET23a) and
pET23a::vdhHis
were prepared for establishing an expression system for heterologous expression in *E. coli*.

The vdh gene was amplified starting with gDNA of *Amycolatopsis* sp. ATCC 39116 by PCR using "Phusion Hot Start II High-Fidelity DNA Polymerase" (Finnzymes, Espoo, Finland). Primers were

```
vdh_for_RBS_NdeI
                                           (SEQ ID NO: 8)
(5'-AAAAcatatgAAACCTCGCGCATCAGGAG-3')
and vdh_rev_XhoI
                                           (SEQ ID NO: 9)
(5'-AAAActcgagAGAACTGGCGCTGGTGCTTCGT-3')
(lower case letters indicate new restriction
sites).
```

The PCR product was isolated preparatively and digested with NdeI and XhoI. An 1.6 kbp NdeI/XhoI fragment was obtained and ligated with a correspondingly treated pET23a plasmid.

*E. coli* Mach1 was transformed with the ligated plasmid; transformants with the hybrid plasmid pET23a::vdh (5150 bp) were identified by selection for ampicillin resistance and were confirmed genotypically.

Cloning was verified by sequencing of the relevant area.

Another hybrid plasmid was obtained accordingly to produce VDH of *Amycolatopsis* sp. ATCC 39116 with a C-terminal-fused $His_6$-tag in *E. coli*. Instead of vdh_rev_XhoI vdh_rev_ohneStop_XhoI (5'-AAAActcgag-GAACGGGTAGCCGGCGACGT-3') (SEQ ID NO: 10) was used as primer.

The resulting 1.5 kbp PCR fragment contained the $vdh_{ATCC\ 39116}$ gene without its native stop codon (TGA);

after ligation with pET23a the gene contained at its 3' end a sequence coding for a His$_6$-tag.

Regulation of the vdh$_{ATCC\ 39116}$ gene in the selected vector system useful for expression of heterologous proteins in *E. coli* was via an inducible T7 promoter system. Suitable expression strains were thus required. Hybrid plasmids pET23a::vdh and pET23a::vdhHis were prepared from transformants of *E. coli* Mach1 and then transformed into a number of expression strains of *E. coli*. The expression strains were *E. coli* BL21(DE3), *E. coli* Rosetta-gami B(DE3) pLysS, *E. coli* Rosetta 2(DE3) pLysS and *E. coli* HMS174(DE3) with the respective hybrid plasmid.

Example 2

Nucleotide Sequence of vdh$_{ATCC\ 39116}$ and Characterization of the Corresponding Gene Product The DNA sequence of the vdh$_{ATCC\ 39116}$ gene is shown in FIG. 2 (SEQ ID NO: 4; nucleotide sequence of the vdh gene of *Amycolatopsis* sp. ATCC 39116.); G+C content is 73.6 mol %. A putative Shine-Dalgarno sequence (AGGAG) is five nucleotides upstream of the GTG start codon of the vdh$_{ATCC\ 39116}$ gene. The identified vdh$_{ATCC\ 39116}$ gene is not in a cluster of further genes whose gene products are involved in the metabolization of ferulic acid in *Amycolatopsis* sp. ATCC 39116.

The amino acid sequence of vanillin dehydrogenase (VDH) of *Amycolatopsis* sp. ATCC 39116 is shown in FIG. 3 (amino acid sequence of vanillin dehydrogenase (VDH) of *Amycolatopsis* sp. ATCC 39116; SEQ ID NO: 5).

The theoretical molecular weight of the protein is 50.6 kDa calculated based on the 486 amino acids sequence derived from the vdh$_{ATCC\ 39116}$ gene. The amino acid sequence of VDH shows homologies with other aldehyde dehydrogenases of various origins.

Example 3

Biotransformation of Vanillin by Recombinant *E. coli* Strains

To ascertain an enzymatic function of the VDH gene product of vdh$_{ATCC\ 39116}$ the gene was expressed heterologously in *E. coli*. Recombinant strains of *E. coli* BL21(DE3) with hybrid plasmids pET23a::vdh and pET23a::vdhHis respectively were grown over night in plain 250 ml flasks with 50 ml LB and 100 µg/ml ampicillin at 30° C. and 100 rpm. Cells were harvested by centrifugation at 4000×g for 20 min, they were washed twice using 100 mM potassium phosphate buffer (pH 7.0) and resuspended in 50 ml modified MSM or HR-medium containing 100 µg/ml ampicillin and 14 mM vanillin. Cultures were incubated at 30° C. for a total of 8 h.

For quantitative determination of metabolites samples were taken under aseptic conditions. Sampled culture supernatants were analyzed via HPLC. As a negative control cultures of *E. coli* BL21(DE3) (pET23a) were treated identically.

Figure 4:
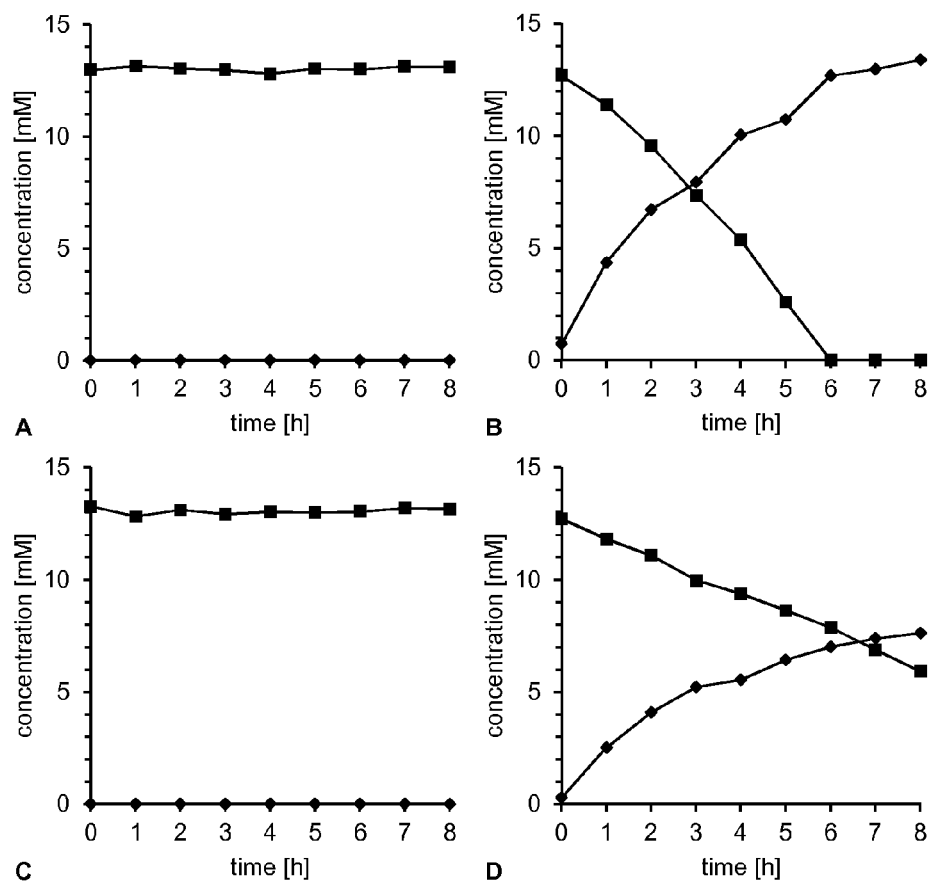
FIG. 4 shows the development of vanillin metabolization in recombinant *E. coli* BL21 (OE3) comprising the vdh gene of *Amycolatopsis* sp. ATCC 39116.

FIG. 4 (Biotransformation of vanillin by recombinant *E. coli* BL21(DE3) comprising the vdh gene of *Amycolatopsis* sp. ATCC 39116) shows the development of vanillin metabolization ((■) vanillin; (♦) vanillic acid; (A) Incubation of *E. coli* BL21(DE3) (pET23a) in modified MSM and vanillin (negative control); (B) biotransformation of vanillin by *E. coli* BL21(DE3) (pET23a::vdh) in modified MSM; (C) incubation of *E. coli* BL21(DE3) (pET23a) in HR-medium and vanillin (negative control); (D) biotransformation of vanillin by *E. coli* BL21(DE3) (pET23a::vdh) in HR-medium).

The negative control (plasmid without vdh$_{ATCC\ 39116}$) did not show a reduction of vanillin concentration and no detectable vanillic acid.

Increasing concentrations of vanillic acid in culture supernatants of *E. coli* BL21(DE3) (pET23a::vdh) indicated functional expression of vdh$_{ATCC\ 39116}$. Conversion of vanillin started instantaneously in both media, vanillic acid was detectable after 1 h. In a culture based on modified MSM all vanillin was consumed within 6 h. Maximum concentration of vanillic acid was 13.4 mM and was obtained after 8 h. Using HR-medium no stimulating effect of yeast extract was observed, contrary to the findings of Civolani et al. 2000. Maximum concentration of vanillic acid was 7.6 mM after 8 h of cultivation. Vanillin was not fully consumed in this period. Molar yield of vanillic acid was 59.9% relative to total vanillin concentration. Cell density as determined by OD$_{600\ nm}$ measurement was comparable in all cultures.

The results confirm rapid and complete oxidation of vanillin to vanillic acid at a substrate concentration of 14 mM by *E. coli* BL21(DE3) (pET23a::vdh) in stationary growth phase.

Further experiments lead to the conclusion that induction by addition of 0.6 mM isopropyl-β-D-thiogalactopyranoside (IPTG) had no influence on the development of biotransformation (data not shown). No significant differences were observed in the biotransformation of vanillin to vanillic acid by *E. coli* BL21(DE3) (pET23a::vdhHis) (data not shown).

In a corresponding assay using 14 mM vanillic acid as a substrate no conversion of vanillic acid by *E. coli* BL21 (DE3) (pET23a), *E. coli* BL21(DE3) (pET23a::vdh) and *E. coli* BL21(DE3) (pET23a::vdhHis) was observed (data not shown).

Example 4

Heterologous Expression of Vanillin Dehydrogenase in *E. coli*, Functional Characterization of the Corresponding Gene Product and its Purification To ascertain functional expression of vdh of *Amycolatopsis* sp. ATCC 39116 in various expression strains VDH activity in the soluble fraction—obtained from crude extracts of *E. coli* BL21(DE3), *E. coli* Rosetta-gami B(DE3) pLysS, *E. coli* Rosetta 2(DE3) pLysS and *E. coli* HMS174 (DE3) having the corresponding hybrid plasmid—was determined.

Strains were cultivated in 400 ml LB with 100 µg/ml ampicillin and further antibiotics as required by the expression strain at 30° C. and 100 rpm until an OD$_{600\ nm}$ of 0.8 was reached. IPTG was added to 200 ml of these cultures to a final concentration of 0.6 mM; the remaining culture was not induced. After further incubation of cultures at 30° C. for 4 h, cells were harvested by centrifugation at 4000×g for 20 min and washed with 100 mM potassium phosphate buffer (pH 7.0). The soluble fraction was obtained and used for determination of VDH activity.

VDH activity of recombinant strains of *E. coli* having the hybrid plasmid pET23a::vdh after induction by the addition of 0.6 mM IPTG are shown in table 5. Presence of vanillic acid was confirmed by HPLC analysis of the reaction mixtures.

TABLE 5

Specific activities of VDH in recombinant strains of
E. coli having the plasmid pET23a::vdh.
Specific activities are given in units per mg protein.

| strain | specific VDH activity [U/mg protein] |
|---|---|
| E. coli BL21(DE3) (pET23a::vdh) | 0.144 ± 0.007 |
| E. coli Rosetta-gami B(DE3) pLysS (pET23a::vdh) | 0.030 |
| E. coli Rosetta 2(DE3) pLysS (pET23a::vdh) | 0.017 |
| E. coli HMS174(DE3) (pET23a::vdh) | 0.102 ± 0.002 |

Figure 5:
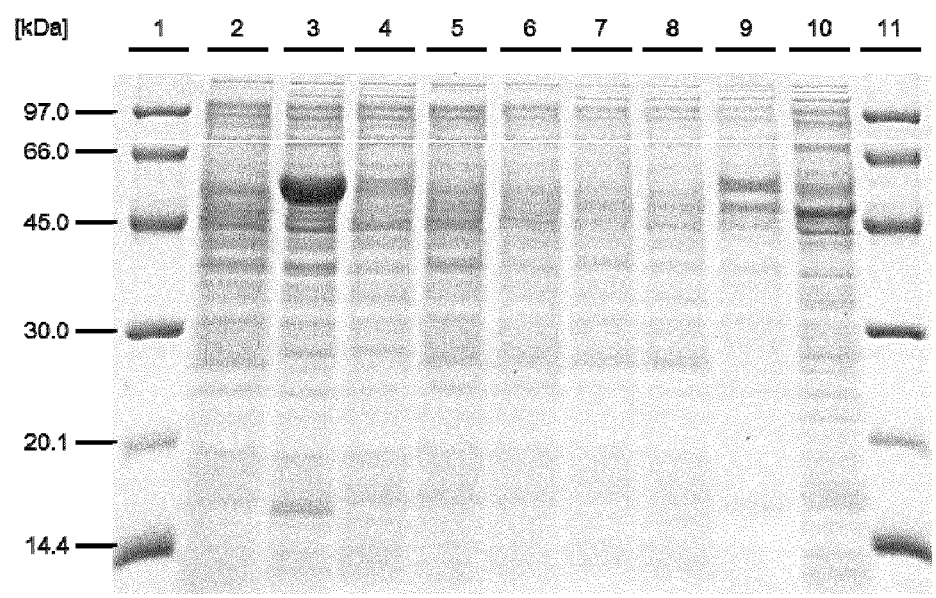
FIG. 5 shows an electropherogram after discontinuous SDS-PAGE to compare VDH synthesis in recombinant strains of *E. coli* having hybrid plasmid pET23a::vdh.

A SDS-PAGE analysis was performed to make the amount of VDH in the soluble fractions comparable and to determine the apparent molecular weight of the $vdh_{ATCC\ 39116}$ gene product (cf. FIG. 5 (electropherogram after discontinuous SDS-PAGE to compare VDH synthesis in recombinant strains of E. coli having hybrid plasmid pET23a::vdh); samples were separated in a 12.5% (w/v) SDS polyacrylamide gel and coloured using Serve Blue G. Lane 1 and 11: 8 µl molecular weight marker; lane 2: 25 µg crude extract of E. coli BL21(DE3) (pET23a); lane 3: 25 µg crude extract of E. coli BL21(DE3) (pET23a::vdh); lane 4: 25 µg soluble fraction of E. coli BL21(DE3) (pET23a::vdh); lane 5: 25 µg crude extract of E. coli Rosetta-gami B(DE3) pLysS (pET23a::vdh); lane 6: 25 µg soluble fraction of E. coli Rosetta-gami B(DE3) pLysS (pET23a::vdh); lane 7: 25 µg crude extract of E. coli Rosetta 2(DE3) pLysS (pET23a::vdh); lane 8: 25 µg soluble fraction of E. coli Rosetta 2(DE3) pLysS (pET23a::vdh); lane 9: 25 µg crude extract of E. coli HMS174(DE3) (pET23a::vdh); lane 10: 25 µg soluble fraction of E. coli HMS174(DE3) (pET23a::vdh)).

Figure 6:
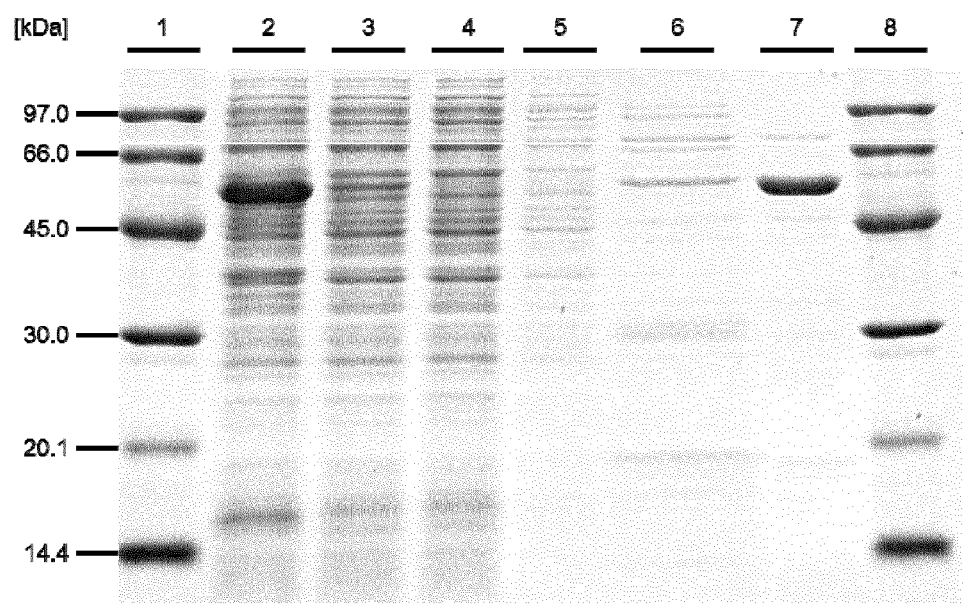
FIG. 6 shows an electropherogram after discontinuous SOS-PAGE for detection of heterologous expression of vdh in *E. coli* and purification via His6-tag.

A prominent protein band of 54.0±2 kDa was detected in SDS-PAGE analysis of crude extracts and soluble fractions of E. coli BL21(DE3) (pET23a::vdh) and E. coli HMS174 (DE3) (pET23a::vdh) (cf. FIG. 5). This size corresponds neatly with the calculated molecular weight of the VDH protein. This result was confirmed by an analysis of the enzyme purified via a $His_6$-tag, wherein a single band was obtained (cf. FIG. 6 (electropherogram after discontinuous SDS-PAGE for detection of heterologous expression of vdh in E. coli and purification via His6-tag): Lane 1 and 8: 8 µl molecular weight marker; lane 2: 25 µg crude extract of E. coli BL21(DE3) (pET23a::vdhHis); lane 3: 25 µg soluble fraction of E. coli BL21(DE3) (pET23a::vdhHis); lane 4: 25 µg flow-through of purification; lane 5: 10 µg first wash step of purification; lane 6: 10 µg fourth wash step of purification; lane 7: 10 µg rebuffered eluate). The enzyme was purified from E. coli BL21(DE3) (pET23a::vdhHis) via the $His_6$-tag and rebuffered in potassium phosphate buffer (pH 7.1). Purified VDH had a specific activity of 0.072 U/mg protein.

E. coli BL21(DE3) (pET23a::vdh) and E. coli BL21(DE3) (pET23a::vdhHis) were selected as preferred strains for synthesis of VDH of Amycolatopsis sp. ATCC 39116 in E. coli due to the amount of heterologously expressed VDH in the soluble fraction and also due to the VDH activity in the soluble fraction.

Example 5

Generating a VDH-deletion Mutant of Amycolatopsis sp. ATCC 39116 (Amycolatopsis sp. ATCC 39116 Δvdh::KmR)

A precise knockout of vdh was accomplished via homologous recombination by replacing the native vdh-gene against a kanamycin resistance cassette. For this, the chromosomal flanking regions upstream and downstream of vdh in the genome were amplified using the following oligonucleotides:

upstream region:

vdhLF_for3
(SEQ ID NO: 11)
(5'-TCGTACTTCGCGGTGATCTCGTGG-3')

and vdhLF_rev_KmR
(SEQ ID NO: 12)
(5'-GACGAGTTCTTCTGACGCGCGGCGGGG-3');

downstream region:

vdhRF_for_PromKmR
(SEQ ID NO: 13)
(5'-CCAGCTGGCAATTCCTGTCACTCCTGATGC-3')

and vdhRF_rev3
(SEQ ID NO: 14)
(5'-TTGCAGTCCTTTGTAGAGCGACACG-3').

Additionally the kanamycin resistance cassette of the plasmid pRLE6 was amplified using KmR_rev_vdhLF
(SEQ ID NO: 15)
(5'-CGCCCCCGCCGCGCGTCAGAAGAACTCGTC-3')

and

PromKmR_for_vdhRF
(SEQ ID NO: 16)
(5'-GCATCAGGAGTGACAGGAATTGCCAGCTGG-3').

The resulting fragments were purified and combined in a subsequent fusion-PCR using primers vdhLF_for 3 and vdhRF_rev3.

The resulting fragment vdhLF_KmR_vdhRF combined the upstream and downstream region of vdh with the kanamycin resistance cassette and this linear fragment was transferred into Amycolatopsis sp. ATCC 39116 by direct mycelia transformation as described elsewhere (Priefert et al. 2002). This procedure was performed to allow a homologous recombination and deletion of the chromosomal vdh gene by exchanging it against the kanamycin resistance cassette from the previously generated linear (and not replicable) PCR fragment.

Transformants of Amycolatopsis sp. ATCC 39116 were selected on solid Caso-medium containing 100 µg/ml kanamycin.

Gene replacement was analyzed via diagnostic PCR with different primer combinations showing a specific integration of the kanamycin resistance cassette into the vdh-locus. Furthermore the resulting PCR-fragments were verified by PCR, restriction analysis and sequencing.

The general principle is shown in the following scheme:

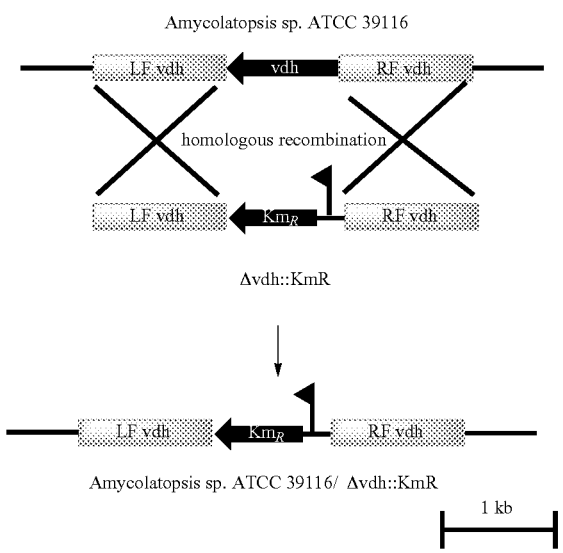

Amycolatopsis sp. ATCC 39116/ Δvdh::KmR

The above scheme shows the generation of a chropmosomal vdh-deletion mutant by homologous recombination (LFvdh, left region downstram of the complete vdh gene; RFvdh, region upstream of the complete vdh gene) with a linear PCR-fragment (Δvdh::Km$^R$). The chromosomal vdh gene is exchanged against a kanamycin resistance marker (Km$^R$).

Further details regarding the aforementioned methods are well known to a person skilled in the art (see e.g. list of references below).

Example 6

Biotransformation of Ferulic Acid by Resting Cells of Amycolatopsis sp. ATCC 39116 and Amycolatopsis sp. ATCC 39116 Δvdh::KmR (Deletion Mutant)

Biotransformation experiments using resting cells of Amycolatopsis sp. ATCC 39116 and Amycolatopsis sp. ATCC 39116 Δvdh::KmR with ferulic acid as sole carbon source were performed in the stationary growth phase. For an appropriate preculture the cells were cultivated in 2×250 ml mL of TSB-media at 42° C. and 150 rpm for 24 h in Erlenmeyer flasks. The used cells for this example had a final optical density (400 nm) of 2.69±0.11. These cells were harvested (at 4000×g, 4° C., 15 min) within the stationary growth phase, washed twice with 100 mM potassium phosphate buffer (pH 7.5) and resuspended in an appropriate volume of the resting cell buffer. The experiment was carried out in two separate 2l-bioreactors with a total potassium phosphate buffer volume of 500 ml. Ferulic acid was added at the beginning of the biotransformation from sterile stock solutions, in the following concentrations: 0.68 g/l (wildtype) and 0.69 g/l (mutant Δvdh::KmR). In this experimental setup a calculated cell dry mass of 0.4 g/l (Amycolatopsis sp. ATCC 39116 Δvdh::KmR) and 0.7 g/l (Amycolatopsis sp. ATCC 39116) was used.

The following figures represent the experimental results from the previous described biotransformation example in a 2l-biorector scale using resting cells of Amycolatopsis sp. ATCC 39116 and Amycolatopsis ATCC39116 Δvdh::KmR.

The following figures display the concentration of selected aromatic compounds during the biotransformation using ferulic acid as carbon source. Additionally, the synthesized products vanillin and vanillic acid were monitored in a chronological sequence.

Figure 7:
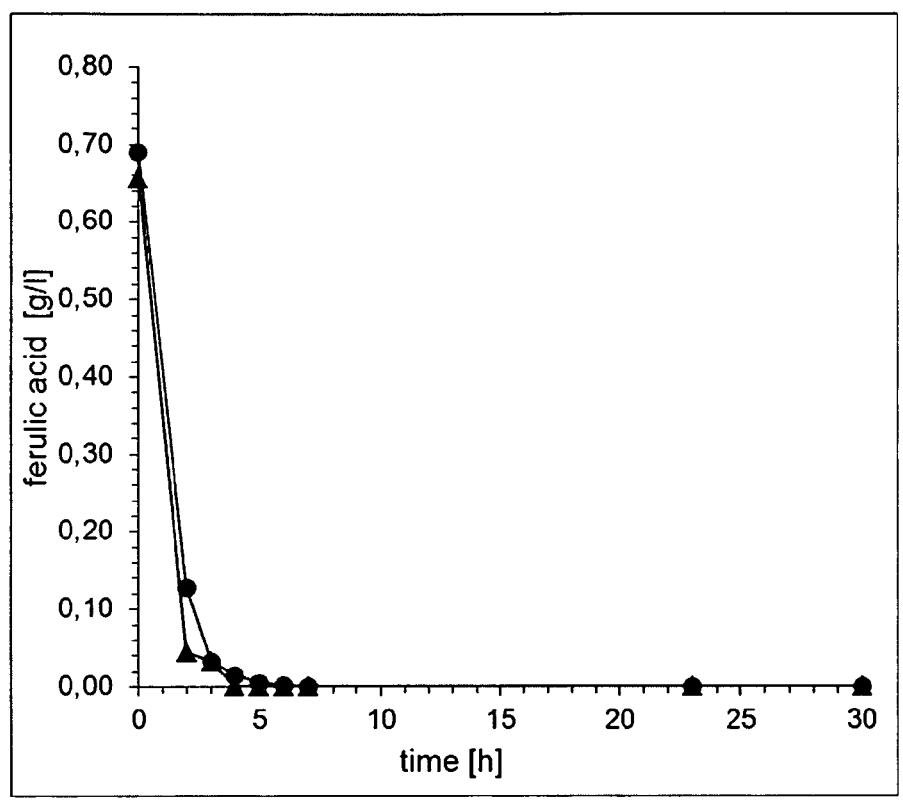
FIG. 7 shows the biotransformation of ferulic acid using cells of *Amycolatopsis* sp. ATCC 39116 and *Amycolatopsis* sp. ATCC 39116 L/vdh::KmR in the stationary growth phase (resting cells). The figure depicts the HPLC-determined concentration and consumption of added ferulic acid (0 h) in a chronological sequence.

FIG. 7 shows the biotransformation of ferulic acid using cells of Amycolatopsis sp. ATCC 39116 (▲) and Amycolatopsis sp. ATCC 39116 Δvdh::KmR (●) in the stationary growth phase (resting cells). The following figure depicts the HPLC-determined concentration and consumption of the uniquely added ferulic acid (0 h) in a chronological sequence.

Figure 8:
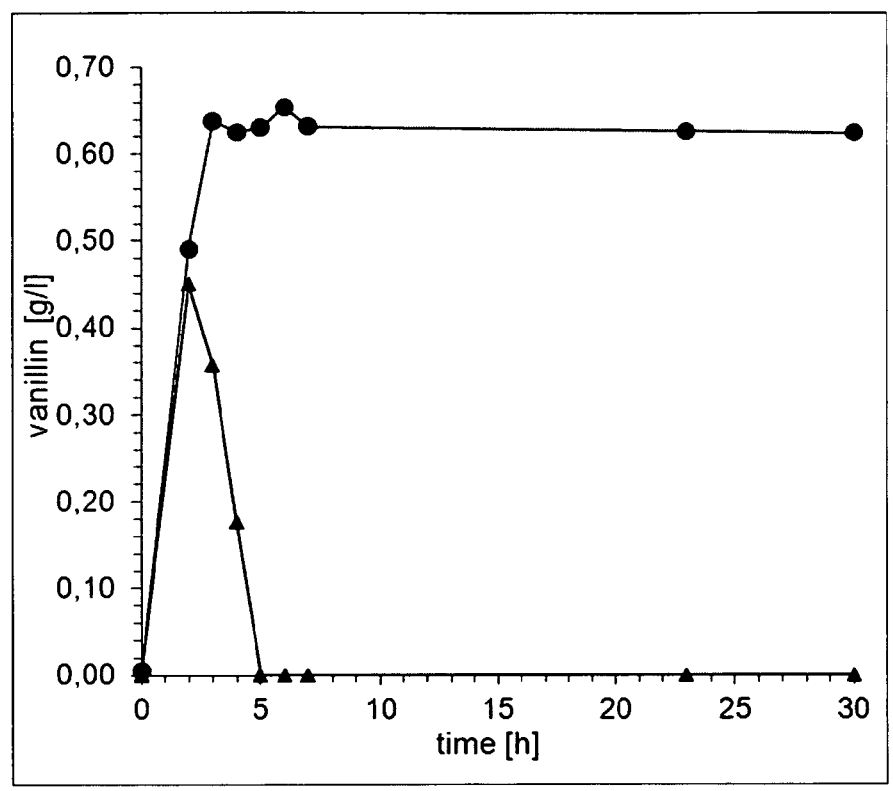
FIG. 8 shows the biotransformation of ferulic acid (to vanillin) using cells of *Amycolatopsis* sp. ATCC 39116 and *Amycolatopsis* sp. ATCC 39116 Llvdh::KmR in the stationary growth phase (resting cells). The figure depicts the HPLC-determined concentration of the synthesized vanillin in a chronological sequence.

FIG. 8 shows the biotransformation of ferulic acid (to vanillin) using cells of Amycolatopsis sp. ATCC 39116 (▲) and Amycolatopsis sp. ATCC 39116 Δvdh::KmR (●) in the stationary growth phase (resting cells). The following figure depicts the HPLC-determined concentration of the synthesized vanillin in a chronological sequence.

Figure 9:
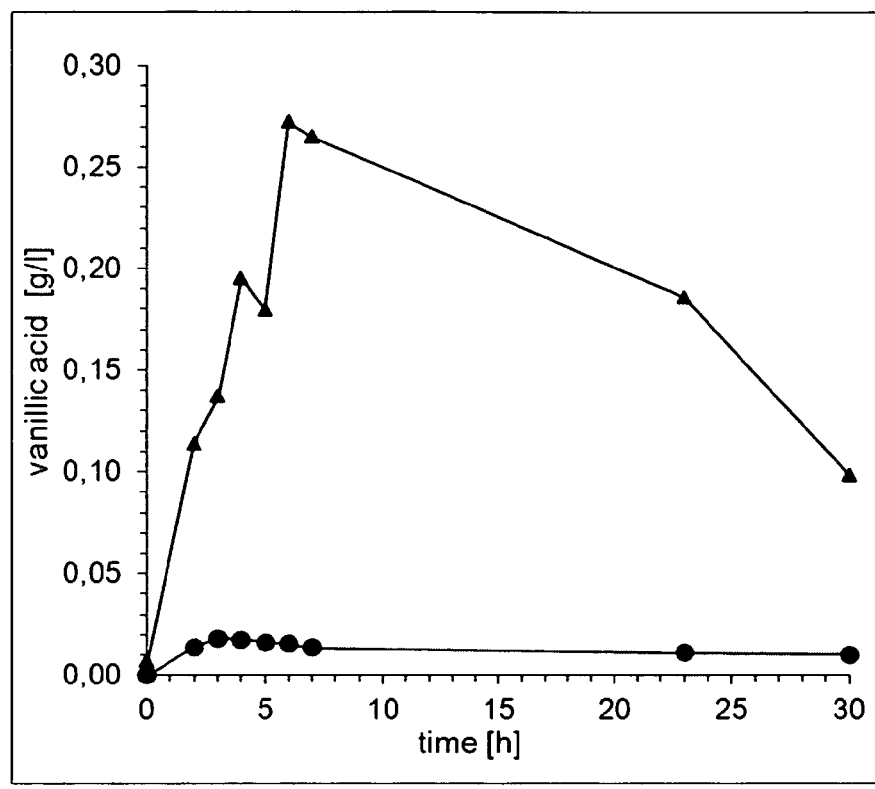
FIG. 9 shows the biotransformation of ferulic acid using cells of *Amycolatopsis* sp. ATCC 39116 and *Amycolatopsis* sp. ATCC 39116 Llvdh::KmR in the stationary growth phase (resting cells). The figure depicts the HPLC-determined concentration of the synthesized vanillic acid in a chronological sequence.

FIG. 9 shows the biotransformation of ferulic acid using cells of Amycolatopsis sp. ATCC 39116 (▲) and Amycolatopsis sp. ATCC 39116 Δvdh::KmR (●) in the stationary growth phase (resting cells). The following figure depicts the HPLC-determined concentration of the synthesized vanillic acid in a chronological sequence.

The presented results show that a deletion of the vanillin dehydrogenase coding gene (vdh) in Amycolatopsis sp. ATCC 39116 has a significant impact on the synthesis and accumulation of vanillin and vanillic acid. Initially, it could be demonstrated that there was no significant effect in the utilization of ferulic acid as sole carbon source between the wild type and mutant strain (see FIG. 7).

The experimental data exhibit, that after a final vanillin concentration was reached (six hours after the experimental beginning) using the vdh-deletion mutant no significant decrease in the vanillin concentration was observed over the entire period (see [6.2]). In contrast to this, the Amycolatopsis sp. ATCC 39116 wildtype strain was only able to synthesize small amounts of vanillin at the beginning of the experiment with a subsequent entire metabolic consumption of vanillin (see FIG. 8).

Finally, the synthesis of vanillic acid (from vanillin) was illustrated in figure [6.3]. Because of the native and active vanillin-dehydrogenase (Vdh) in the wildtype strain Amycolatopsis sp. ATCC 39116 a rising concentration of vanillic acid (as a product of the further metabolized vanillin) was detected. The accumulated vanillic acid concentration was 15-fold higher than the vanillic acid concentration synthesized by the vdh-deletion mutant Amycolatopsis sp. ATCC 39116 Δvdh::KmR. This mutant showed a significant and permanent lower vanillic acid concentration compared to the wildtype strain (see FIG. 9). The continuously decreasing concentration of vanillic acid after 6 hours in the experimental approach using the wildtype strain might be explained by a further metabolisation because of the limited or missing primary carbon source (ferulic acid).

LIST OF REFERENCES/LITERATURE

Altschul S F, Wootton J C, Gertz E M, Agarwala R, Morgulis A, Schäffer A A, Yu Y K (2005) Protein database searches using compositionally adjusted substitution matrices. FEBS J 272: 5101-5109.

Altschul S F, Madden T L, Schäffer A A, Zhang J, Zhang Z, Miller W, Lipman D J (1997) Gapped BLAST and PSI- BLAST: a new generation of protein database search programs. *Nucleic Acids Res* 25: 3389-3402.

Bare G, Swiatkowski T, Moukil A, Gerday C, Thonart P (2002) Purification and characterization of a microbial dehydrogenase: a vanillin:NAD(P)$^+$ oxidoreductase. *Appl Biochem Biotechnol* 98-100: 415-428.

Beck E, Ludwig G, Auerswald E A, Reiss B, Schaller H (1982) Nucleotide sequence and exact localization of the neomycin phosphotransferase gene from transposon Tn5. *Gene* 19: 327-336.

Bendtsen J D, Nielsen H, von Heijne G, Brunak S (2004) Improved prediction of signal peptides: SignalP 3.0. *J Mol Biol* 340: 783-795.

Bradford M M (1976) A rapid and sensitive method for the quantitation of microgram quantities of protein utilizing the principle of protein dye binding. *Anal Biochem* 72: 248-254.

Civolani C, Barghini P, Roncetti A R, Ruzzi M, Schiesser A (2000) Bioconversion of ferulic acid into vanillic acid by means of a vanillate-negative mutant of *Pseudomonas fluorescens* strain BF13. *Appl Environ Microbiol* 66: 2311-2317.

Furukawa H, Morita H, Yoshida T, Nagasawa T (2003) Conversion of isoeugenol into vanillic acid by *Pseudomonas putida* 158 cells exhibiting high isoeugenol-degrading activity. *J Biosci Bioeng* 96: 401-403.

Gasson M J, Kitamura Y, McLauchlan W R, Narbad A, Parr A J, Parsons E L, Payne J, Rhodes M J, Walton N J (1998) Metabolism of ferulic acid to vanillin. A bacterial gene of the enoyl-SCoA hydratase/isomerase superfamily encodes an enzyme for the hydration and cleavage of a hydroxycinnamic acid SCoA thioester. *J Biol Chem* 273: 4163-4170.

Gasteiger E, Gattiker A, Hoogland C, Ivanyi I, Appel R D, Bairoch A (2003) ExPASy: The proteomics server for in-depth protein knowledge and analysis. *Nucleic Acids Res* 31: 3784-3788.

Ghosh S, Sachan A, Sen S K, Mitra A (2007) Microbial transformation of ferulic acid to vanillic acid by *Streptomyces sannanensis* MTCC 6637. *J Ind Microbiol Biotechnol* 34: 131-138.

Greated A, Lambertsen L, Williams P A, Thomas C M (2002) Complete sequence of the IncP-9 TOL plasmid pWW0 from *Pseudomonas putida*. *Environ Microbiol* 4: 856-871.

Hall T A (1999) BioEdit: a user-friendly biological sequence alignment editor and analysis program for Windows 95/98/NT. *Nucleic Acids Symposium Series* 41: 95-98.

Hanahan D (1983) Studies on transformation of *Escherichia coli* with plasmids. *J Mol Biol* 166: 557-580.

Hidalgo E, Chen Y M, Lin E C C, Aguilar J (1991) Molecular cloning and DNA sequencing of the *Escherichia coli* K-12 ald gene encoding aldehyde dehydrogenase. *J Bacteriol* 173: 6118-6123.

Kroll J, Klinter S, Steinblichel A (2011) A novel plasmid addiction system for large-scale production of cyanophycin in *Escherichia coli* using mineral salts medium. *Appl Microbiol Biotechnol* 89: 593-604.

Laemmli U K (1970) Cleavage of structural proteins during the assembly of the head of bacteriophage T4. *Nature* 227: 680-685.

Martinez-Cuesta M D C, Payne J, Hanniffy S B, Gasson M J, Narbad A (2005) Functional analysis of the vanillin pathway in a vdh-negative mutant of *Pseudomonas fluorescens* AN103. *Enzyme Microb Technol* 37: 131-138.

Masai E, Yamamoto Y, Inoue T, Takamura K, Hara H, Kasai D, Katayama Y, Fukuda M (2007) Characterization of ligV essential for catabolism of vanillin by *Sphingomonas paucimobilis* SYK-6. *Biosci Biotechnol Biochem* 71: 2487-2492.

Mitsui R, Hirota M, Tsuno T, Tanaka M (2010) Purification and characterization of vanillin dehydrogenases from alkaliphile *Micrococcus* sp. TA1 and neutrophile *Burkholderia cepacia* TM1. *FEMS Microbiol Lett* 303: 41-47.

Narbad A, Gasson M J (1998) Metabolism of ferulic acid via vanillin using a novel CoA-dependent pathway in a newly-isolated strain of *Pseudomonas fluorescens*. *Microbiology* 144: 1397-1405.

Nelson K E, Weinel C, Paulsen I T, Dodson R J, Hilbert H, Martins dos Santos V A, Fouts D E, Gill S R, Pop M, Holmes M, Brinkac L, Beanan M, DeBoy R T, Daugherty S, Kolonay J, Madupu R, Nelson W, White O, Peterson J, Khouri H, Hance I, Chris Lee P, Holtzapple E, Scanlan D, Tran K, Moazzez A, Utterback T, Rizzo M, Lee K, Kosack D, Moestl D, Wedler H, Lauber J, Stjepandic D, Hoheisel J, Straetz M, Heim S, Kiewitz C, Eisen J A, Timmis K N, Dusterhoft A, Tummler B, Fraser C M (2002) Complete genome sequence and comparative analysis of the metabolically versatile *Pseudomonas putida* KT2440. *Environ Microbiol* 4: 799-808.

McLeod M P, Warren R L, Hsiao W W, Araki N, Myhre M, Fernandes C, Miyazawa D, Wong W, Lillquist A L, Wang D, Dosanjh M, Hara H, Petrescu A, Morin R D, Yang G, Stott J M, Schein J E, Shin H, Smailus D, Siddiqui A S, Marra M A, Jones S J, Holt R, Brinkman F S, Miyauchi K, Fukuda M, Davies J E, Mohn W W, Eltis L D (2006) The complete genome of *Rhodococcus* sp. RHA1 provides insights into a catabolic powerhouse. *Proc Natl Acad Sci USA* 103: 15582-15587.

Oliynyk M, Samborskyy M, Lester J B, Mironenko T, Scott N, Dickens S, Haydock S F, Leadlay P F (2007) Complete genome sequence of the erythromycin-producing bacterium *Saccharopolyspora erythraea* NRRL23338. *Nat Biotechnol* 25: 447-453.

Overhage J, Priefert H, Rabenhorst J, Steinbüchel A (1999) Biotransformation of eugenol to vanillin by a mutant of *Pseudomonas* sp. strain HR199 constructed by disruption of the vanillin dehydrogenase (vdh) gene. *Appl Microbiol Biotechnol* 52: 820-828.

Parke D, Ornston L N (2003) Hydroxycinnamate (hca) catabolic genes from *Acinetobacter* sp. strain ADP1 are repressed by HcaR and are induced by hydroxycinnamoyl-coenzyme A thioesters. *Appl Environ Microbiol* 69: 5398-5409.

Perestelo F, Dalcon M A, de la Fuente G (1989) Production of vanillic acid from vanillin by resting cells of *Serratia marcescens*. *Appl Environ Microbiol* 55: 1660-1662.

Plaggenborg R, Overhage J, Loos A, Archer J A C, Lessard P, Sinskey A J, Steinbüchel A, Priefert H (2006) Potential of *Rhodococcus* strains for biotechnological vanillin production from ferulic acid and eugenol. *Appl Microbiol Biotechnol* 72: 745-755.

Plaggenborg R, Overhage J, Steinbüchel A, Priefert H (2003) Functional analyses of genes involved in the metabolism of ferulic acid in *Pseudomonas putida* KT2440. *Appl Microbiol Biotechnol* 61: 528-535.

Plaggenborg R, Steinbüchel A, Priefert H (2001) The coenzyme A-dependent, non-β-oxidation pathway and not direct deacetylation is the major route for ferulic acid degradation in *Delftia acidovorans*. *FEMS Microbiol Lett* 205: 9-16.

Pometto A L, Crawford D L (1983) Whole-cell bioconversion of vanillin to vanillic acid by *Streptomyces viridosporus*. *Appl Environ Microbiol* 45: 1582-1585.

Priefert H, Rabenhorst J, Steinbüchel A (1997) Molecular characterization of genes of *Pseudomonas* sp. strain HR199 involved in bioconversion of vanillin to protocatechuate. *Bacteriol* 179: 2595-2607.

Priefert H, Achterholt S, Steinbüchel A (2002) Transformation of the Pseudonocardiaceae *Amycolatopsis* sp. strain HR167 is highly dependent on the physiological state of the cells. *Appl Microbiol Biotechnol* 58: 454-460.

Priefert H, Rabenhorst J, Steinbüchel A (2001) Biotechnological production of vanillin. *Appl Microbiol Biotechnol* 56: 296-314.

Rabenhorst J (1996) Production of methoxyphenol-type natural aroma chemicals by biotransformation of eugenol with a new *Pseudomonas* sp. *Appl Microbiol Biotechnol* 46: 470-474.

Rabenhorst J, Hopp R (1997) Process for the preparation of vanillin and suitable microorganisms. European Patent 0761817.

Saitou N, Nei M (1987) The neighbor-joining method: a new method for reconstructing phylogenetic trees. *Mol Biol Evol* 4: 406-425.

Sambrook J, Russell D (2001) Molecular cloning: A laboratory manual. Cold Spring Harbor Laboratory Press.

Schlegel H G, Kaltwasser H, Gottschalk G (1961) Ein Submersverfahren zur Kultur wasserstoffoxydierender Bakterien: Wachstumsphysiologische Untersuchungen. *Archiv Mikrobiol* 38: 209-222.

Sekine M, Tanikawa S, Omata S, Saito M, Fujisawa T, Tsukatani N, Tajima T, Sekigawa T, Kosugi H, Matsuo Y, Nishiko R, Imamura K, Ito M, Narita H, Tago S, Fujita N, Harayama S (2006) Sequence analysis of three plasmids harboured in *Rhodococcus erythropolis* strain PR4. *Environ Microbiol* 8: 334-346.

Silby M W, Cerdeno-Tarraga A M, Vernikos G S, Giddens S R, Jackson R W, Preston G M, Zhang X X, Moon C D, Gehrig S M, Godfrey S A, Knight C G, Malone J G, Robinson Z, Spiers A J, Harris S, Challis G L, Yaxley A M, Harris D, Seeger K, Murphy L, Rutter S, Squares R, Quail M A, Saunders E, Mavromatis K, Brettin T S, Bentley S D, Hothersall J, Stephens E, Thomas C M, Parkhill J, Levy S B, Rainey P B, Thomson N R (2009) Genomic and genetic analyses of diversity and plant interactions of *Pseudomonas fluorescens*. *Genome Biol* 10: R51.

Stentelaire C, Lesage-Meessen L, Oddou J, Bernard O, Bastin G, Colonna Ceccaldi B, Asther M (2000) Design of a fungal bioprocess for vanillin production from vanillic acid at scalable level by *Pycnoporus cinnabarinus*. *Journal of Bioscience and Bioengineering* 89: 223-230.

Venturi V, Zennaro F, Degrassi G, Okeke B C, Bruschi C V (1998) Genetics of ferulic acid bioconversion to protocatechuic acid in plant-growth-promoting *Pseudomonas putida* WCS358. *Microbiology* 144: 965-973.

Zhao W, Zhong Y, Yuan H, Wang J, Zheng H, Wang Y, Cen X, Xu F, Bai J, Han X, Lu G, Zhu Y, Shao Z, Yan H, Li C, Peng N, Zhang Z, Zhang Y, Lin W, Fan Y, Qin Z, Hu Y, Zhu B, Wang S, Ding X, Zhao G (2010) Complete genome sequence of the rifamycin SV-producing *Amycolatopsis mediterranei* U32 revealed its genetic characteristics in phylogeny and metabolism. *Cell Res* 20: 1096-1108.

The invention claimed is:

1. A method for producing a product selected from the group consisting of vanillin, feruloyl-CoA, ferulic acid, coniferyl aldehyde and coniferyl alcohol, comprising adding an educt selected from the group consisting of eugenol, coniferyl alcohol, coniferyl aldehyde and ferulic acid to a microorganism of order Actinomycetales and genus *Amycolatopsis*, wherein the microorganism does not comprise a gene coding for a vanillin dehydrogenase having at least 90% sequence similarity with SEQ ID NO 1, 2, or 3, or comprises an inactivated vanillin dehydrogenase gene having at least 90% sequence similarity with SEQ ID NO 1, 2, or 3.

2. The method according to claim 1, wherein the vanillin dehydrogenase has the amino acid sequence of SEQ ID 1, 2 or 3.

3. The method according to claim 1, wherein the microorganism comprises a vanillin dehydrogenase gene inactivated by an insert or a deletion.

4. The method according to claim 1, wherein the microorganism further comprises one or more of:
an eugenol hydroxylase gene of *Pseudomonas* sp. DSMZ 7063, a vanillyl alcohol oxidase gene of *Penicillium simplicissimium*, an eugenol oxidase gene of *Rhodococcus jostii* RHA1,
a coniferyl alcohol dehydrogenase gene of *Pseudomonas* sp. DSMZ 7063, an aromatic alcohol dehydrogenase gene (adhA; accession number AB213394) of *Rhodococcus opacus* TKN14, an aryl alcohol dehydrogenase gene of *Acinetobacter* sp. ADP1, an aryl alcohol dehydrogenase gene of *Rhodococcus erythropolis* PR4, *Lactobacillus plantarum* WCFS1 (lp_3054; accession number CAB69495) and *Gordonia polyisoprenivorans* Kd2 (adhA, accession number ZP 09272609.1), a coniferyl aldehyde dehydrogenase of *Pseudomonas* sp. DSMZ 7063, a benzaldehyde dehydrogenase of *Acinetobacter* sp. ADP1, an aldehyde-dehydrogenase of *Arabidopsis thaliana* (ALDH2C4, accession number NM 113359.3), a benzaldehyde dehydrogenase of *Pseudomonas putida* mt-2 (XyIC, accession number U15151.1), a dodecanal dehydrogenase *Gluconobacter oxydans* 521H (accession number YP 190934), a feruloyl-CoA-synthetase of *Pseudomonas* sp. DSMZ 7063, or an enoyl-CoA-hydratase/aldolase of *Pseudomonas* sp. DSMZ 7063.

5. A microorganism of order Actinomycetales and genus *Amycolatopsis*, wherein the microorganism does not comprise a gene coding for a vanillin dehydrogenase having a sequence with 90% sequence similarity with SEQ ID NO 1, 2, or 3, or microorganism comprises an inactivated vanillin dehydrogenase gene having at least 90% sequence similarity with SEQ ID NO 1, 2, or 3.

6. The microorganism of claim 5, wherein the vanillin dehydrogenase has the amino acid sequence of SEQ ID 1, 2 or 3.

7. The microorganism of claim 5, wherein the microorganism comprises a vanillin dehydrogenase gene inactivated by an insert or a deletion.

8. The microorganism of claim 5, wherein the microorganism comprises a gene selected from the group consisting of:

an eugenol hydroxylase gene of *Pseudomonas* sp. DSMZ 7063, a vanillyl alcohol oxidase gene of *Penicillium simplicissimium*, and an eugenol oxidase gene of *Rhodococcus jostii* RHA1, a coniferyl alcohol dehydrogenase gene of *Pseudomonas* sp. DSMZ 7063, an aromatic alcohol dehydrogenase gene (adhA; accession number AB213394) of *Rhodococcus opacus* TKN14, an aryl alcohol dehydrogenase gene of *Acinetobacter* sp. ADP1, an aryl alcohol dehydrogenase gene of *Rhodococcus erythropolis* PR4, *Lactobacillus plantarum* WCFS1 (Ip_3054; accession number CAB69495) and *Gordonia polyisoprenivorans* Kd2 (adhA, accession number ZP 09272609.1), a coniferyl aldehyde dehydrogenase of *Pseudomonas* sp. DSMZ 7063, a benzaldehyde dehydrogenase of *Acinetobacter* sp. ADP1, an aldehyde-dehydrogenase of *Arabidopsis thaliana* (ALDH2C4, accession number NM 113359.3), a benzaldehyde dehydrogenase of *Pseudomonas putida* mt-2 (XyIC, accession number U15151.1), and a dodecanal dehydrogenase *Gluconobacter oxydans* 521H (accession number YP 190934), a feruloyl-CoA-synthetase of *Pseudomonas* sp. DSMZ 7063, or an enoyl-CoA-hydratase/aldolase of *Pseudomonas* sp. DSMZ 7063.

9. The microorganism of claim 5, wherein the microorganism comprises one or more of the following modifications:

the gene for vanillin dehydrogenase is inactivated by an insertion of an antibiotic resistance gene into the gene coding for vanillin dehydrogenase;

the microorganism additionally comprises a vanillyl alcohol oxidase gene of *Penicillium simplicissimium* and/or an eugenol hydroxylase gene of *Rhodococcus jostii* RHA1;

and optionally the microorganism additionally comprises a coniferyl alcohol dehydrogenase gene of *Pseudomonas* sp. DSMZ 7063 and a coniferyl aldehyde dehydrogenase of *Pseudomonas* sp. DSMZ 7063.

10. A method for producing a substance selected from the group consisting of:

vanillin from any educt elected from eugenol, coniferyl alcohol, coniferyl aldehyde, ferulic acid and feruloyl-CoA, feruloyl-CoA from any educt elected from eugenol, coniferyl alcohol, coniferyl aldehyde and ferulic acid, ferulic acid from any educt elected from eugenol, coniferyl alcohol and coniferyl aldehyde, coniferyl aldehyde from any educt elected from eugenol and coniferyl alcohol, and coniferyl alcohol from eugenol as educt, comprising the steps of:

providing the microorganism of claim 5, and exposing the microorganism to an educt.

11. The method of claim 10, wherein the substance is vanillin from any of eugenol, coniferyl alcohol, coniferyl aldehyde, ferulic acid and feruloyl-CoA, wherein the vector comprises:

an eugenol hydroxylase gene of *Pseudomonas* sp. DSMZ 7063, a vanillyl alcohol oxidase gene of *Penicillium simplicissimium*, an eugenol oxidase gene of *Rhodococcus jostii* RHA1, a coniferyl alcohol dehydrogenase gene of *Pseudomonas* sp. DSMZ 7063, an aromatic alcohol dehydrogenase gene (adhA; accession number AB213394) of *Rhodococcus opacus* TKN14, an aryl alcohol dehydrogenase gene of *Acinetobacter* sp. ADP1, an aryl alcohol dehydrogenase gene of *Rhodococcus erythropolis* PR4, *Lactobacillus plantarum* WCFS1 (Ip_3054; accession number CAB69495) and *Gordonia polyisoprenivorans* Kd2 (adhA, accession number ZP 09272609.1), a coniferyl aldehyde dehydrogenase of *Pseudomonas* sp. DSMZ 7063, a benzaldehyde dehydrogenase of *Acinetobacter* sp. ADP1, an aldehyde-dehydrogenase of *Arabidopsis thaliana* (ALDH2C4, accession number NM 113359.3), a benzaldehyde dehydrogenase of *Pseudomonas putida* mt-2 (XyIC, accession number U15151.1), a dodecanal dehydrogenase *Gluconobacter oxydans* 521H (accession number YP 190934), a feruloyl-CoA-synthetase of *Pseudomonas* sp. DSMZ 7063, or an enoyl-CoA-hydratase/aldolase of *Pseudomonas* sp. DSMZ 7063.

12. A method of constructing microorganism of claim 5 comprising:

providing a microorganism of order Actinomycetales and genus *Amycolatopsis*, wherein the microorganism does not comprise a gene coding for a vanillin dehydrogenase having at least 90% sequence similarity with SEQ ID NO 1, 2, or comprises an inactivated vanillin dehydrogenase gene having at least 90% sequence similarity with SEQ ID NO 1, 2, or 3, transforming the microorganism with an omega element to inactivate a gene coding for a vanillin dehydrogenase, and selecting a recombinant obtained by the transformation step.

13. The method of claim 12 further comprising:

transforming the microorganism with a vector and;

selecting the microorganism comprising the vector;

wherein the vector comprises:

an eugenol hydroxylase gene of *Pseudomonas* sp. DSMZ 7063, a vanillyl alcohol oxidase gene of *Penicillium simplicissimium*, an eugenol oxidase gene of *Rhodococcus jostii* RHA1, a coniferyl alcohol dehydrogenase gene of *Pseudomonas* sp. DSMZ 7063, an aromatic alcohol dehydrogenase gene (adhA; accession number AB213394) of *Rhodococcus opacus* TKN14, an aryl alcohol dehydrogenase gene of *Acinetobacter* sp. ADP1, an aryl alcohol dehydrogenase gene of *Rhodococcus erythropolis* PR4, *Lactobacillus plantarum* WCFS1 (lp_3054; accession number CAB69495) and *Gordonia polyisoprenivorans* Kd2 (adhA, accession number ZP 09272609.1), a coniferyl aldehyde dehydrogenase of *Pseudomonas* sp. DSMZ 7063, a benzaldehyde dehydrogenase of *Acinetobacter* sp. ADP1, an aldehyde-dehydrogenase of *Arabidopsis thaliana* (ALDH2C4, accession number NM 113359.3), a benzaldehyd dehydrogenase of *Pseudomonas putida* mt-2 (XyIC, accession number U15151.1), a dodecanal dehydrogenase *Gluconobacter oxydans* 521H (accession number YP 190934), a feruloyl-CoA-synthetase of *Pseudomonas* sp. DSMZ 7063, or an enoyl-CoA-hydratase/aldolase of *Pseudomonas* sp. DSMZ 7063.

14. The microorganism of claim 1, wherein the microorganism is deposited as ATCC 39116.

15. The microorganism of claim 5, wherein the microorganism is deposited as ATCC 39116.

* * * * *